(12) United States Patent
Taylor-Smith

(10) Patent No.: US 7,433,118 B2
(45) Date of Patent: Oct. 7, 2008

(54) BRIDGED POLYSESQUIOXANE HOST MATRICES CONTAINING LANTHANIDES CHELATED BY ORGANIC GUEST LIGANDS, AND METHODS OF MAKING SUCH MATRICES

(75) Inventor: Ralph E. Taylor-Smith, Watchung, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 1191 days.

(21) Appl. No.: 10/606,690

(22) Filed: Jun. 26, 2003

(65) Prior Publication Data

US 2004/0263952 A1    Dec. 30, 2004

(51) Int. Cl.
*H01S 3/00* (2006.01)
*C08G 79/00* (2006.01)

(52) U.S. Cl. .......................... 359/342; 528/9
(58) Field of Classification Search ............... 359/341.5, 359/342; 528/9
See application file for complete search history.

(56) References Cited

U.S. PATENT DOCUMENTS

| | | | |
|---|---|---|---|
| 5,116,703 A | 5/1992 | Badesha et al. | |
| 5,231,156 A | 7/1993 | Lin | |
| 5,321,102 A | 6/1994 | Loy et al. | |
| 5,384,376 A | 1/1995 | Tunney et al. | |
| 5,412,043 A | 5/1995 | Novak et al. | |
| 5,527,871 A | 6/1996 | Tani et al. | |
| 5,719,976 A | 2/1998 | Henry et al. | |
| 5,739,180 A | 4/1998 | Taylor-Smith | |
| 5,965,202 A | 10/1999 | Taylor-Smith et al. | |
| 5,971,610 A * | 10/1999 | Kolodner et al. | ............ 374/161 |
| 6,184,968 B1 | 2/2001 | Taylor-Smith | |
| 6,187,427 B1 | 2/2001 | Taylor-Smith et al. | |
| 6,268,089 B1 | 7/2001 | Chandross et al. | |
| 6,313,219 B1 | 11/2001 | Taylor-Smith | |

OTHER PUBLICATIONS

Ainslie, A Review of the Fabrication and Properties of Erbium-Doped Fibers for Optical Amplifiers, Journal of Lightwave Technology, Feb. 1991, pp. 220-227, vol. 9, No. 2.

Choi et al., Amorphous Polysilsesquioxanes as a Confinement Matrix for Quantum-Sized Particle Growth: Size Analysis and Quantum Size Effect of CdS Particles Grown in Porous Polysilsesquioxanes, J. Phys. Chem., 1994, pp. 3207-3214, vol. 98, No. 12.

Choi et al., New Materials for Synthesis of Quantum-Sized Semiconductors and Transition-Metal Particles: Microporous Polysilsesquioxanes as a Confinement Matrix for Particle Growth, Chem. Mater., 1993, pp. 1067-1069, vol. 5, No. 8.

(Continued)

*Primary Examiner*—Randy Gulakowski
*Assistant Examiner*—Robert Loewe

(57) ABSTRACT

Bridged polysesquioxane compositions comprising: a bridged polysesquioxane host matrix comprising sesquioxane moieties and organic moieties, the sesquioxane moieties comprising a metallic element, the organic moieties interposed between sesquioxane moieties; and a guest molecule comprising a lanthanide atom; at least some of the organic moieties comprising a substituent selected from the group consisting of electron withdrawing functional groups and electron donating functional groups. Processes for making such bridged polysesquioxane compositions. Gain media and active materials for upconversion lasers comprising such bridged polysesquioxane compositions. Light can be amplified by fluorescence emissions from the bridged polysesquioxane compositions.

8 Claims, 21 Drawing Sheets

OTHER PUBLICATIONS

Choi et al., New Procedures for the Preparation of CdS and Heterogeneous Cr/CdS Phases in Hybrid Xerogel Matrices: Pore Structure Analysis and Characterization, J. Phys. Chem., 1995, pp. 4720-4732, vol. 99, No. 13.

Choi et al., Preparation of Nano-Sized Chromium Clusters and Intimate Mixtures of Chromium/CdS Phases in a Porous Hybrid Xerogel by an Internal Doping Method, J. Am. Chem. Soc., 1994, pp. 9052-9060, vol. 116, No. 20.

Dejneka et al., Rare-Earth-Doped Fibers for Telecommunications Applications, MRS Bulletin, Sep. 1999, pp. 39-45, vol. 24, No. 9.

Dutton, Optical Devices, Understanding Optical Communications, pp. 189-229.

Empedocles et al., Photoluminescence Spectroscopy of Single CdSe Nanocrystallite Quantum Dots, Physical Review Letters, Oct. 28, 1996, pp. 3873-3876, vol. 77, No. 18.

Gapontsev et al., Erbium Glass Lasers and Their Applications, Optics and Laser Technology, Aug. 1982, pp. 189-196.

Hines et al., Synthesis and Characterization of Strongly Luminescing ZnS-Capped CdSe Nanocrystals, J. Phys. Chem., 1996, pp. 468-471, vol. 100, No. 2.

Kagan et al., Electronic Energy Transfer in CdSe Quantum Dot Solids, Physical Review Letters, Feb. 26, 1996, pp. 1517-1520, vol. 76, No. 9.

Kik et al., Erbium-Doped Optical-Waveguide Amplifiers on Silicon, MRS Bulletin, Apr. 1998, pp. 48-54.

Krishnaswamy et al., Optical Properties of Polymer Waveguides Dispensed on an Erbium/Ytterbium Codoped Glass, IEEE Journal of Selected Topics in Quantum Electronics, Jun. 1996, pp. 373-377, vol. 2, No. 2.

Lochhead et al., Rare-Earth Clustering and Aluminum Codoping in Sol-Gel Silica: Investigation Using Europium(III) Fluorescence Spectroscopy, Chem. Mater., 1995, pp. 572-577, vol. 7, No. 3.

Loy et al., Sol-Gel Synthesis of Hybrid Organic-Inorganic Materials: Hexylene- and Phenylene-Bridged Polysiloxanes, Chem. Mater., 1996, pp. 656-663, vol. 8, No. 3.

Murray et al., Self-Organization of CdSe Nanocrystallites into Three-Dimensional Quantum Dot Superlattices, Science, Nov. 24, 1995, pp. 1335-1338, vol. 270.

Steckl et al., Photonic Applications of Rare-Earth-Doped Materials, MRS Bulletin, Sep. 1999, pp. 16-17, vol. 24, No. 9.

Taylor-Smith et al., Erbium-Doped Polysilsesquioxane Molecular Composite Systems, Proceedings of the American Chemical Society Division of Polymeric Materials: Science and Engineering, Aug. 2000, pp. 237-238, vol. 83, Publisher: American Chemical Society.

Urquhart, Review of Rare Earth Doped Fibre Lasers and Amplifiers, IEE Proceedings, Dec. 1988, pp. 385-407, vol. 135, Pt. J, No. 6.

Zyskind et al., Erbium-Doped Fiber Amplifiers and the Next Generation of Lightwave Systems, AT&T Technical Journal, Feb. 1992, pp. 53-62.

Desurvire, The Golden Age of Optical Fiber Amplifiers, Physics Today, Jan. 1994, pp. 20-27, vol. 47.

Digiovanni, Materials Aspects of Optical Amplifiers, Mat. Res. Soc. Symp. Proc., 1992, pp. 135-142, vol. 244, Publisher: Materials Research Society.

Hanna, Fibre Lasers, Solid State Lasers: New Developments and Applications, 1993, pp. 231-245, Edited by Inguscio et al., Publisher: Plenum Press, Published in: New York.

Lee et al., Ion Clustering and Crystallization of Sol-Gel-Derived Erbium Silicate Glass, J. Mater. Sci. Lett., 1994, pp. 615-617, vol. 13.

Loy et al., Bridged Polysilsesquioxanes: Highly Porous Hybrid Organic-Inorganic Materials, Chem. Rev., 1995, pp. 1431-1442, vol. 95.

Sanchez et al., Design of Hybrid Organic-Inorganic Materials Synthesized via Sol-Gel Chemistry, New J. Chem., Oct. 1994, pp. 1007-1047, vol. 18.

Stone et al., In Situ Dehydroxylation in $Eu^{3+}$-Doped Sol-Gel Silica, Chem. Mater., 1997, pp. 2592-2598, vol. 9.

Jin, Tetsuro, et al., "Luminescence properties of lanthanide complexes incorporated into sol-gel derived inorganic-organic composite materials", *J. Non-Cryst. Solids*, vol. 223, pp. 123-132 (Elsevier Science B.V., 1998).

Reisfeld, Renata, et al., "Rare earth ions, their spectroscopy of cryptates and related complexes in sol-gel glasses", *Optical Materials*, vol. 24, pp. 1-13 (Elsevier B.V., 2003).

Trejo-Valdez, M., et al., "Aerosol-gel deposition of photocurable ORMOSIL films doped with a terbium complex", *Optical Materials*, vol. 25, pp. 179-184 (Elsevier B.V., 2004).

Park, Oun-Ho, et al., "Indirect excitation of $Er^{3+}$ in sol-gel hybrid films doped with an erbium complex", *Appl. Phys. Lett.*, vol. 82, No. 17, pp. 2787-2789 (Amer. Instit. Phys., Apr. 28, 2003).

Strek, W., et al., "Optical properties of Eu(III) chelates trapped in silica gel glasses", *Optical Materials*, vol. 13, pp. 41-48 (Elsevier Science B.V., 1999).

Fan, Xianping, et al., "Luminescence behavior of the europium (III) complexes with hexafluoroacetylacetonate in the ORMOSIL matrices", *Mat. Sci. & Eng'g*, vol. B100, pp. 147-151 (Elsevier Science B.V., 2003).

* cited by examiner

BRIDGED POLYSESQUIOXANE HOST MATRICES CONTAINING LANTHANIDES CHELATED BY ORGANIC GUEST LIGANDS, AND METHODS OF MAKING SUCH MATRICES

FIELD OF THE INVENTION

The present invention relates to the field of lanthanide containing materials that can be excited with applied radiation and that are useful in optical devices and systems.

BACKGROUND OF THE INVENTION

Erbium doped-fiber amplifier (EDFA) systems are well known as useful for amplifying an electromagnetic radiation signal, for example a photonic optical signal. In such amplifier system configurations, input and output waveguides for carrying such an optical signal are interposed by gain media constituted by an inorganic glass amplifier waveguide fiber which is doped with a lanthanide element. The lanthanides have incomplete inner electron orbitals that facilitate excitation of electrons into higher energy levels by applied photonic energy referred to as pumping radiation. When the optical signal is carried into the amplifier waveguide fiber and itself applies further photonic energy to such lanthanides, the excited electrons are triggered to return to lower energy states and to simultaneously release photons. The release of these photons is referred to as fluorescence. Repeated excitation and fluorescent emission takes place as a chain reaction within the amplifier waveguide fiber, modulated by the optical signal. As a result, the output waveguide carries an amplified copy of the optical signal received from the input waveguide. Luminescence generally cannot be generated by direct excitation of lanthanide atoms due to their poor ability to absorb light. Organic chromophores can be provided to absorb the light energy and transfer it to nearby lanthanide atoms.

Optical waveguide fibers typically are fabricated from conventional inorganic glass materials such as silicon dioxide or silica, including dopants that generate an appropriate refractive index profile and otherwise enable the optical waveguide fibers to carry an optical signal. Inorganic glass is particularly the material of choice for fabricating optical fibers for long haul optical telecommunications systems. Inorganic silica glass materials, for example, have excellent thermal stability, and on a molecular scale are essentially free of light scattering and phase separation. A given optical fiber incorporated in a long haul system can traverse distances measured in miles without requiring any interconnection splicing of fibers. However, interconnection splicing of inorganic glass optical fibers, when ultimately required, is a delicate operation. The core of a typical inorganic glass optical fiber is very small, making the mutual lateral alignment of optical fiber ends a tedious process requiring specialized connecting devices and procedures. Connections are typically made by installing optical fiber connectors on the fiber ends, and then assembling the connectors together.

In short haul applications, optical waveguide fiber lengths between connection points may be short, due to complex mesh network interconnections of optical waveguide fibers, together with the needs for a variety of interposed components such as EDFAs, add drop multiplexers, optical cross connects, and other components. Hence, required optical waveguide fiber interconnections in short haul applications, such as office local area networks (LANs) and intravehicle mobile communication systems, may proliferate to extremely large magnitudes.

In addition to the labor and connector device costs inherent in short haul applications, the cumulative weight of the resulting network nodes can be detrimental in certain applications. For example, in an aircraft equipped with complex networked telecommunications systems, the cumulative weight of the inorganic glass fibers embodied in these systems can be detrimental to the aircraft performance.

Organic plastic optical waveguide fibers are an available alternative to inorganic glass optical waveguide fibers. Organic plastic materials typically have a substantially lower density than does, for example, silicon dioxide. Organic plastic optical waveguide fibers, however, are typically characterized by higher levels of signal attenuation, and inferior mechanical stability, compared with inorganic glass optical waveguide fibers. Organic plastic materials are subject, for example, to creep and other losses of mechanical integrity. They also typically contain compositional impurities and phase separated imperfections that can cause light scattering and attenuation. Organic plastic planar waveguides, to which the same comments apply, are an analogous type of optical transmission architecture. However, organic plastic planar waveguides typically are utilized in optical integrated circuit applications.

As explained above, interconnection splices between inorganic glass optical fibers require careful lateral alignment and specially adapted connectors. In addition to mutual lateral alignment between spliced fibers, the spliced fiber ends must also be aligned at a tolerable distance from each other in order to carry a signal. Fiber ends too close together can lead to impacting of the ends, resulting in fiber misalignment and signal failure, and fiber ends too far apart can also lead to signal failure. Diverse materials have correspondingly diverse coefficients of thermal expansion, typically with adverse consequences from environmental temperature excursions. Accordingly, amplifier waveguide fibers for EDFAs to be used together with inorganic glass optical fibers typically are likewise made from inorganic glass materials to facilitate their interconnection and integration with conventional optical waveguide fiber network systems. However, amplifier waveguide fibers made from inorganic glass materials are not well suited to make EDFAs to be interconnected with organic plastic optical waveguide fibers, for example due to the mismatch in thermal expansion coefficients.

Inorganic glass and organic plastic precursor materials can be combined together by sol-gel technology for use in making polymeric optical fiber waveguides, both for use as signal transmission carriers in long- and short-haul telecommunications and as doped with lanthanides to be employed as gain media in EDFAs and other active devices. The resulting organic/inorganic glass hybrid materials offer properties that are not available from organic or inorganic materials alone. Their coefficients of expansion can be made compatible with those of conventional organic plastic materials. Thus, sol-gel technology constitutes a potential solution to the need for organic plastic optical waveguide fibers that effectively resolve the telecommunication fiber weight problem, and the need for mutually compatible gain media for active devices such as EDFAs. Upconversion lasers are an exemplary further class of active devices in which the active materials can be produced by combining together inorganic glass and organic plastic precursor materials by sol-gel technology.

Sol-gels are produced by condensation of reagents containing —Si—OH groups, with release of water as a byproduct. These reagents can contain any desired organic groups. Since the reactions can be carried out at room temperature, the organic groups can be conserved in the polymerized system. However, a high level of uncondensed hydroxyl groups generally remains in materials prepared by the sol-gel process. Such hydroxyl groups reduce the fluorescence efficiency and shorten the luminescent lifetimes of lanthanide dopant ions in the material, adversely affecting optical signal amplification performance. In addition, there is a tendency for lanthanide ion clustering to occur in sol-gel systems. Ion clustering of lanthanides leads to self quenching of fluorescent emissions between lanthanide atoms that are too close together, reducing the total fluorescence.

Various sol-gel polysesquioxane compositions have been produced, including those doped with lanthanides. However, there is a need for improved polysesquioxane hybrid polymer compositions that are engineered for use as gain media in EDFAs, as active elements in upconversion lasers, and in other active applications. Such improved active hybrid polymeric systems would enable fluorescence at power levels suitable for signal amplification purposes, and address the problem of lanthanide ion clustering. Such active doped hybrid polymer material based systems would also tolerate interconnection of active elements with organic plastic-based optical fibers, facilitating the assembly of organic plastic fiber based telecommunications components, networks and systems. There is also a need for processes for making such polysesquioxane compositions, and for lanthanide doped media fabricated from such compositions that can be used in active devices such as optical fiber amplifiers, upconversion lasers, and other devices requiring elements for generation of lanthanide pumping fluorescent emissions.

SUMMARY OF THE INVENTION

The present invention provides bridged polysesquioxane host matrices having chelated lanthanide atom-containing guest molecules, which are useful in preparing gain media and other active materials for generating fluorescent emissions by applied pumping radiation. Bridged polysesquioxanes are polymers that include covalent bonds between a selected metallic element and oxygen, and that include pairs of atoms of such metallic element that are covalently bonded to an interposed carbon linkage. An exemplary metallic element is silicon; and an exemplary lanthanide is erbium.

In one embodiment according to the present invention, a bridged polysesquioxane composition is provided, comprising: a bridged polysesquioxane host matrix comprising sesquioxane moieties and organic moieties, the sesquioxane moieties comprising a metallic element, the organic moieties interposed between sesquioxane moieties; and a guest molecule comprising a lanthanide atom; at least some of the organic moieties comprising a substituent selected from the group consisting of electron withdrawing functional groups and electron donating functional groups.

In another embodiment according to the present invention, such a bridged polysesquioxane composition is provided, in which at least some of the organic moieties comprise an electron withdrawing functional group. In a further embodiment according to the present invention, such a bridged polysesquioxane composition is provided in which at least some of the organic moieties comprise an electron donating functional group binding the guest molecule. In an additional embodiment according to the present invention, such a bridged polysesquioxane composition is provided in which the metallic element is selected from the group consisting of silicon, aluminum, titanium, zirconium, germanium, and mixtures. In another embodiment according to the present invention, such a bridged polysesquioxane composition is provided in which the bridged polysesquioxane host matrix is a bridged polysilsesquioxane host matrix, and the sesquioxane moieties are silsesquioxane moieties. In a further embodiment according to the present invention, such a bridged polysesquioxane composition is provided in which the polysesquioxane host matrix is produced by polymerization of di(trialkoxy) monomers either comprising at least about 38% by weight of fluorine, or comprising at least eight fluorine atoms. In an additional embodiment according to the present invention, such a bridged polysesquioxane composition is provided that has a fluorescence peak that is capable of amplifying light within at least one wavelength range selected from the group consisting of 900-1000 nanometers, 1260-1360 nanometers, and 1500-1600 nanometers.

In another embodiment according to the present invention, a process for making a bridged polysesquioxane composition is provided, comprising the steps of: providing a bridged polysesquioxane host matrix comprising sesquioxane moieties and organic moieties, the sesquioxane moieties comprising a metallic element, the organic moieties interposed between sesquioxane moieties; and providing a guest molecule comprising a lanthanide atom; at least some of the organic moieties comprising a substituent selected from the group consisting of electron withdrawing functional groups and electron donating functional groups.

In a further embodiment, a gain medium is provided, comprising a polysesquioxane composition according to the present invention. In an additional embodiment, an active material for an upconversion laser is provided, comprising a polysesquioxane composition according to the present invention.

These and other embodiments will become apparent to those skilled in the art from the following detailed description read in conjunction with the appended claims and the drawings attached hereto.

BRIEF DESCRIPTION OF THE DRAWINGS

The present invention will be better understood from reading the following description of non-limiting embodiments, with reference to the attached drawings, wherein below.

It should be emphasized that the drawings are not to scale but are merely schematic representations, and thus are not intended to portray specific dimensions, which may be determined by skilled artisans through examination of the disclosure herein.

DETAILED DESCRIPTION

The present invention relates to bridged polysesquioxane compositions comprising lanthanide atoms, methods for making such compositions, and applications for the use of such compositions. The term "bridged polysesquioxane" is defined as a polymeric system including covalent bonds between a selected metallic element and oxygen, and including pairs of atoms of such metallic element covalently bonded to an interposed carbon linkage. The term "bridged" denotes the presence of such pairs of metallic atoms covalently bonded to an interposed carbon linkage. It is to be understood, however, that the term "bridged polysesquioxane" is not limited to compositions in which every pair of metallic atoms is covalently bonded to an interposed carbon linkage. Rather, some portion or all of such pairs of metallic atoms is so bonded. Suitable metallic elements include, for example, silicon, aluminum, titanium, zirconium and germanium. In one embodiment according to the present invention, the metallic element is silicon, optionally also including other metallic elements as desired. The polysesquioxane composition in that embodiment is referred to as a "polysilsesquioxane." Accordingly, the term "bridged polysilsesquioxane" is defined as a polymeric system including covalent bonds between silicon and oxygen, and including pairs of silicon atoms, some or all of which are covalently bonded to an interposed carbon linkage. Much of the ensuing discussion is presented in the context of polysilsesquioxanes. However, it is to be understood that these teachings can readily be adapted to replacement of silicon in whole or part in any or all of the reagents employed for practice of the invention, by other metallic elements and mixtures detailed above.

Figure 1:
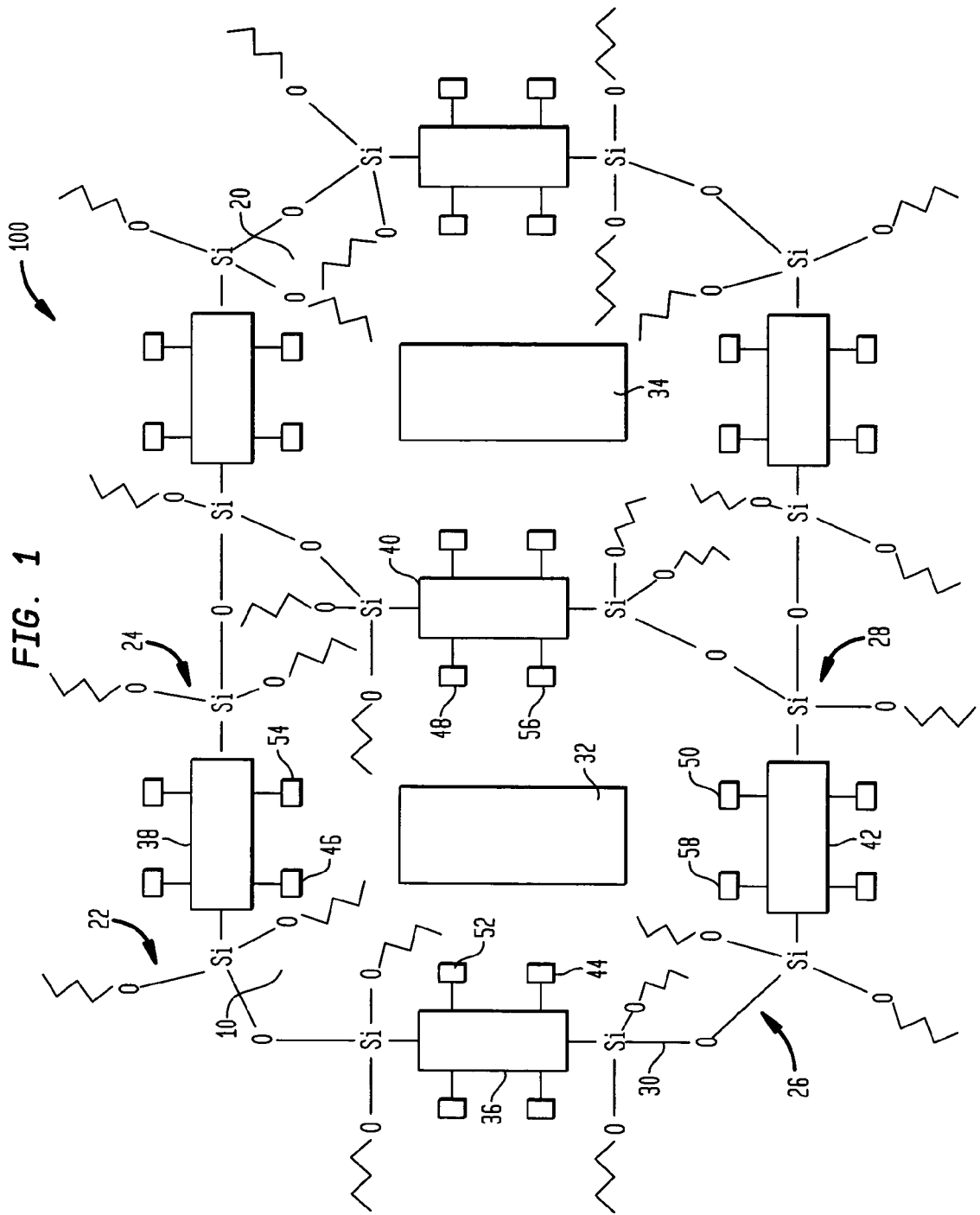
FIG. 1 shows an exemplary embodiment of representative cells of the structure of a bridged polysilsesquioxane composition in accordance with the present invention.

FIG. 1 shows an exemplary embodiment 100 of two representative cells 10 and 20 of the structure of a bridged polysilsesquioxane composition in accordance with the present invention. Referring to cell 10, covalent bonds between silicon and oxygen are shown at the four corners 22, 24, 26 and 28 of the cell, such as exemplary bond 30. Given the presence of these silicon-oxygen bonds at the four corners of cell 10, the representative structure can be infinitely extended in a three dimensional polymeric form, as illustrated by the exemplary adjacent cell 20. This extended structure of cells is linked by silicon-oxygen bonds, in a manner analogous to that of a conventional silicon dioxide inorganic glass or silica.

At the centers of cells 10 and 20 are lanthanide atom-comprising guest molecules 32 and 34, respectively. Exemplary cell 10 further includes four organic moieties 36, 38, 40 and 42. These organic moieties are interposed between and covalently bonded with the four corners 22, 24, 26 and 28 of the cell. Hence, the organic moieties 36, 38, 40 and 42 create a defined space between each of the resulting silsesquioxane moieties located at the four corners 22, 24, 26 and 28 of the cell, and are themselves placed in positions surrounding guest molecule 32.

The organic moieties 36, 38, 40 and 42 further include functional groups 44, 46, 48 and 50, respectively. Each of the functional groups 44, 46, 48 and 50 interacts with the guest molecule 32, and facilitates positioning of the guest molecule 32 within the cell 10. The organic moieties constitute a carbon linkage between the adjacent silicon atoms, thus forming a bridged polysilsesquioxane structure. Accordingly, the cell 10 may be considered to constitute a polysilsesquioxane host matrix for binding with and containing a guest molecule 32. The size of the organic moieties 36, 38, 40 and 42 determines the ultimate size of the cell 10 and hence the porosity of the polysilsesquioxane host matrix. Depending on the size of the organic moieties selected, the pore diameters may range from about 30 Å to about 100 Å, with a corresponding surface area ranging between about 1800 to 1 square meters per gram (g). Small pore sizes are advantageous in minimizing the potential for light scattering.

In one exemplary embodiment, functional groups 44, 46, 48 and 50 are electron donating groups, and guest molecules 32 and 34 are erbium atoms. Erbium has a valence of 3+ and thus can readily accept donated electrons. Hence, functional groups 44, 46, 48 and 50 may donate electrons to facilitate positioning and retention of guest molecule 32 within cell 10. The attractive force generated by this electron donation tends to distribute minimal chelated erbium atoms in each cell, thus reducing the potential for agglomeration. In the absence of this attractive force, phase separation of erbium atoms together into an agglomerated form is more likely to occur. Agglomerated erbium atoms can quench fluorescent emissions from adjacent erbium atoms by cross relaxation or energy transfer, leading to reduced total fluorescence and thus reduced optical amplification potential.

Polysilsesquioxanes are generally produced by sol-gel condensation of silicon alkoxides, silicon hydroxides, and their mixtures. Alkoxide moieties are partially or completely hydrolyzed to yield hydroxide moieties. The carbon-containing silicon hydroxides are then condensed either with each other or with remaining alkoxides, forming —Si—O—Si— bonds with retained carbon. These condensation reactions result in the successive formation of sols, aerogels, and xerogels. As the condensation proceeds, the sol viscosity increases, leading to imperfections in the condensation reaction process. For example, some of the silicon hydroxide moieties may become isolated in the sol or gel, preventing their condensation.

Erbium pumping results in the desired fluorescence emissions as discussed earlier. In particular, erbium exhibits a $^4I_{11/2} \Rightarrow {}^4I_{15/2}$ transition at about 980 nanometers (nm) and a $^4I_{13/2} \Rightarrow {}^4I_{15/2}$ transition at about 1540 nm. Silicon hydroxide bonds have high phonon energy in the range of 3000-3500 centimeters$^{-1}$ (cm$^{-1}$). Silicon hydroxide moieties remaining in the polysilsesquioxane composition quench some of the fluorescent radiation emitted by the erbium through coupling of this high phonon energy. The performance capability of a lanthanide containing gain medium fabricated from the polysilsesquioxane is accordingly reduced.

In one embodiment, the concentration of these uncondensed silicon hydroxide moieties in the bridged polysilsesquioxane matrices containing guest molecules produced according to the present invention is substantially reduced, accordingly reducing the coupling energy of phonons with the lanthanide. As a result, total fluorescent emissions are increased. In a further embodiment according to the present invention, exemplary organic moieties 36, 38, 40 and 42 contain functional groups 52, 54, 56 and 58 which are electron withdrawing groups. Electron withdrawing functional groups 52, 54, 56 and 58 are hydrophobic and repel hydrophilic regions of the composition such as uncondensed —Si—OH moieties. Hence, localized phase separation is induced. As a result of this phase separation, the uncondensed —Si—OH moieties are pushed into closer proximity with each other, thus increasing the potential for their condensation and thus reduction of their concentration in the polysilsesquioxane.

In another embodiment according to the present invention, exemplary organic moieties 36, 38, 40 and 42 contain both electron donating functional groups 44, 46, 48 and 50, as well as electron withdrawing functional groups 52, 54, 56 and 58. These functional groups influence the structure of the bridged polysilsesquioxane composition in the same manner as discussed above, so that condensation of —Si—OH groups is maximized, and the lanthanide atoms are positioned within cells of the polymer to minimize their agglomeration.

Figure 2:
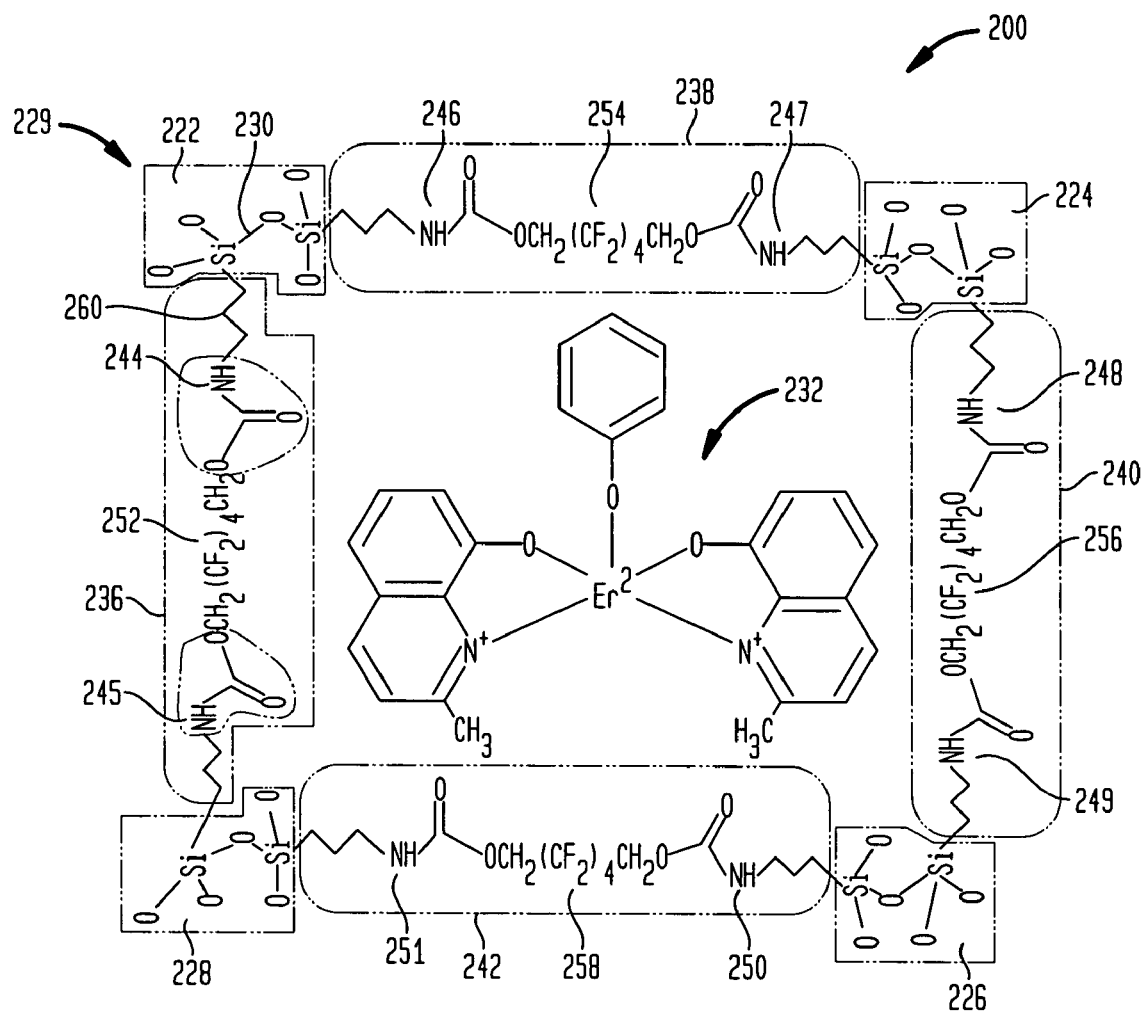
FIG. 2 shows an exemplary embodiment of a representative cell of the structure of another bridged polysilsesquioxane composition in accordance with the present invention.

FIG. 2 shows an exemplary embodiment of a representative cell 200 of the structure of another bridged polysilsesquioxane composition in accordance with the present invention. Covalent bonds between silicon and oxygen are shown at the four corners 222, 224, 226 and 228 of the polysilsesquioxane host matrix generally indicated at 229, such as exemplary bond 230. Given the presence of these silicon-oxygen bonds at the four corners of cell 200, the representative structure can be infinitely extended in a three dimensional polymeric form.

At the center of cell 200 is exemplary erbium atom-comprising guest molecule 232. Guest molecule 232 contains two dehydrogenated 8-hydroxyquinaldine molecules and one dehydrogenated phenol molecule chelated with one erbium atom. Labile electrons from the three resulting oxygen ions and from the two ring nitrogen atoms, together chelated with the erbium atom, reduce the valence of the erbium atom from 3+ to 2–. Hence, the erbium atom is tightly held in place by the aromatic complex. The aromatic moieties absorb photons, and can exchange energy with and thus influence the fluorescence of the erbium atom.

Exemplary cell 200 further includes four organic moieties 236, 238, 240 and 242. These organic moieties are interposed between and covalently bonded with the four corners 222, 224, 226 and 228 of the cell. Hence, the organic moieties 236, 238, 240 and 242 create a defined space between each of the resulting silsesquioxane moieties formed at the four corners 222, 224, 226 and 228 of the cell, and are themselves placed in positions surrounding guest molecule 232.

Exemplary organic moiety 236 includes a pair of electron donating functional urethane groups 244 and 245. Similarly, exemplary organic moieties 238, 240 and 242 include pairs of electron donating functional urethane groups generally indicated at 246 and 247, 248 and 249, and 250 and 251, respectively. Each of the functional urethane groups 244-251 contains two free nitrogen valence electrons that may interact with the guest molecule 232, and that facilitate positioning and retention of the guest molecule 232 within the cell 200.

The exemplary organic moieties 236, 238, 240 and 242 also contain electron-withdrawing functional fluoroalkyl groups generally indicated at 252, 254, 256 and 258. Electron withdrawing functional fluoroalkyl groups 252, 254, 256 and 258 are hydrophobic, and repel hydrophilic regions of the composition such as uncondensed —Si—OH moieties. Hence, localized phase separation is induced to create hydrophobic and hydrophilic regions. As a result of this phase separation, the hydrophilic —Si—OH moieties are pushed away from the hydrophobic organic regions and into closer proximity with each other, thus increasing the potential for their condensation.

Exemplary cell 200 shown in FIG. 2 comprises four organic moieties 236, 238, 240 and 242 interposed between four corners 222, 224, 226 and 228 forming four silsesquioxane moieties. Throughout this discussion, cells similarly comprising four organic moieties are shown and discussed. However, cells may be formed or predominate in a bridged polysilsesquioxane composition according to the present invention that comprise, for example, 3, 5, 6, 7 or more organic moieties and a corresponding number of corners forming silsesquioxane moieties. Although cells comprising only two organic moieties are unlikely to be formed due to steric hindrance considerations, they are contemplated as well.

Figure 3:
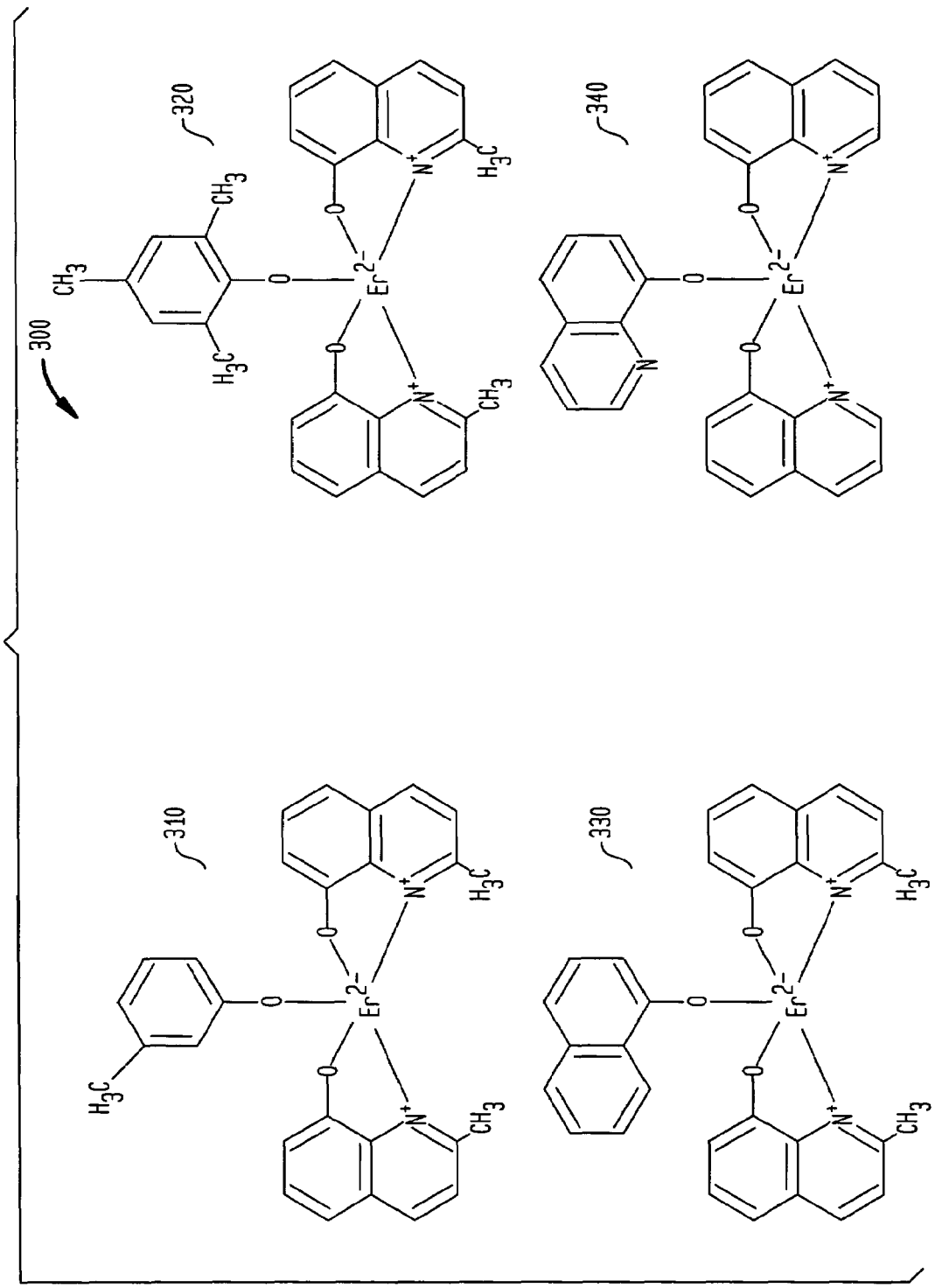
FIG. 3 shows an array of exemplary erbium atom-comprising guest molecules for use in accordance with the present invention.

FIG. 3 shows an array 300 of exemplary erbium atom-comprising guest molecules 310, 320, 330 and 340 that can be substituted for erbium atom-comprising guest molecule 232 within the cell 200. Each of guest molecules 310, 320 and 330 comprises two dehydrogenated 8-hydroxyquinaldine molecules chelated with one erbium atom, as does guest molecule 232. In guest molecule 310, meta-methyl phenol is substituted for the phenol employed in synthesizing erbium atom-comprising guest molecule 232. In guest molecule 320, 2,4,6-trimethylphenol is substituted. In guest molecule 330, hydroxynaphthalene is substituted. Guest molecule 340 comprises three dehydrogenated 8-hydroxyquinoline molecules.

Figure 4:
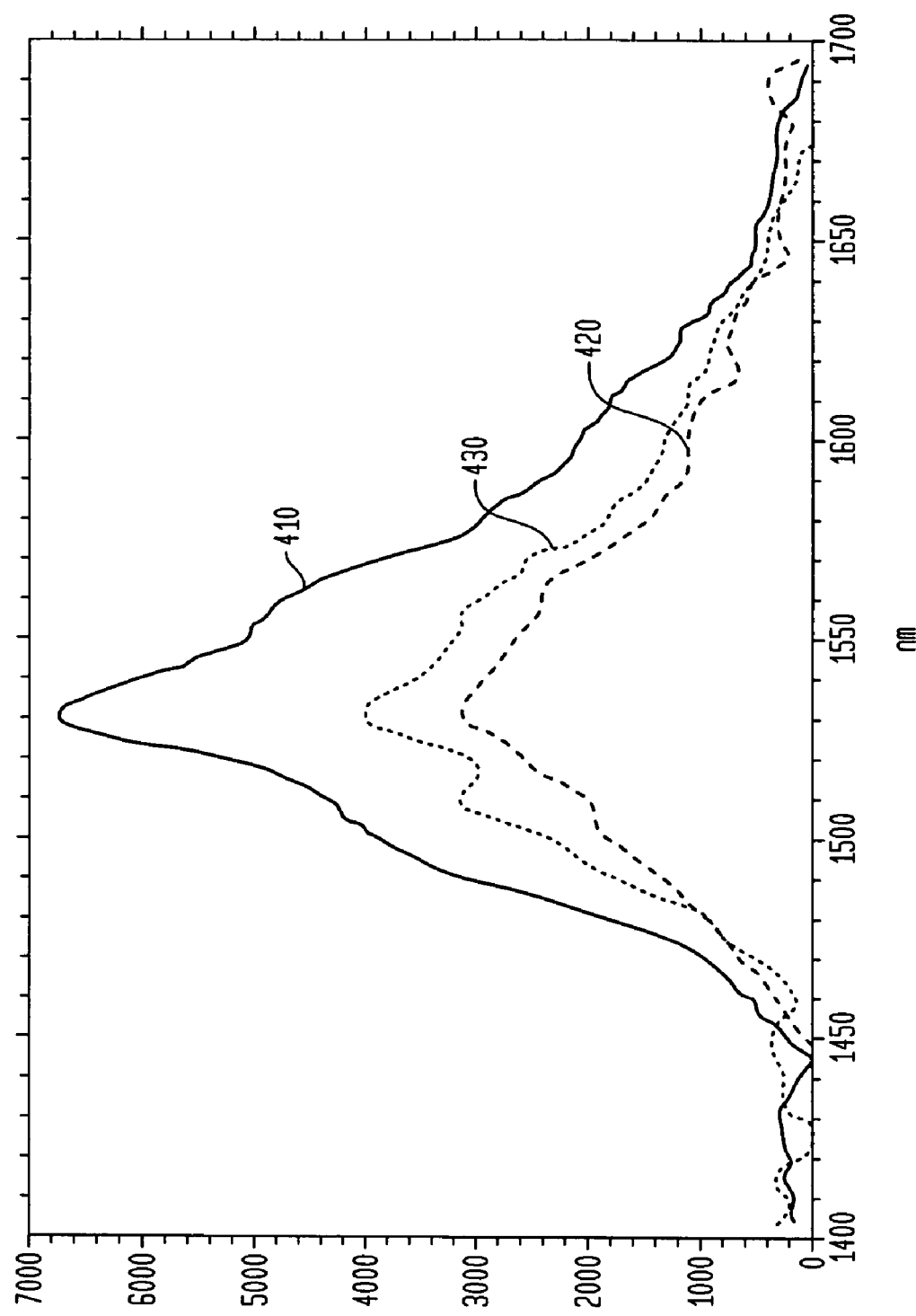
FIG. 4 shows graphed fluorescent emission responses of erbium atom-comprising guest molecules in accordance with the present invention.

FIG. 4 shows the fluorescent emission responses of erbium atom-comprising guest molecules 232, 320 and 340. The vertical axis plots fluorescence intensity in atomic units (a.u.). The horizontal axis plots fluorescence emission wavelengths in nanometers. The data were generated by excitation of samples of the respective erbium atom-comprising guest molecules by the 488 nm line of an argon ion laser at a power density of about 0.5 to about 5 watts per square centimeter. Curves 410, 420 and 430 report the results for erbium atom-comprising guest molecules 232, 320, and 340 respectively. FIG. 4 shows that the strongest fluorescence at about 1550 nm was obtained with erbium atom-comprising guest molecule 232. The strength of the fluorescent emissions generally increases with increasing laser power density within the tested range.

It can be seen that the basic structure of all of guest molecules 232 and 310-340 comprises two dehydrogenated 8-hydroxyquinoline molecules. It is believed that pumping radiation is absorbed by the aromatic moieties in these guest molecules and transferred to the chelated erbium atoms. Hence, these various complex structures exchange energy with and thus further modify the fluorescence behavior of the chelated erbium atom, and can be used to tune such fluorescence as desired for particular applications. Those of ordinary skill in the art will readily modify these exemplary compounds to provide further suitable erbium atom-comprising guest molecules.

Figure 5:
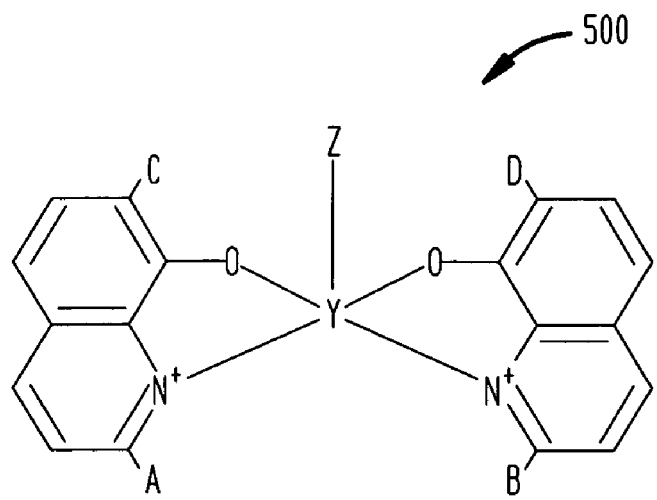
FIGS. 5-7 show exemplary embodiments of classes of lanthanide atom-comprising guest molecules that can be used in accordance with the present invention.

FIG. 5 shows an exemplary embodiment of a class of compounds 500 encompassing guest molecules 232 and 310-340, that can be used in accordance with the present invention. In FIG. 5, A, B, C and D each independently can be hydrogen or -alkyl; Y is a lanthanide atom; and Z is an oxyaryl group. For example, the 8-hydroxyquinolinyl moieties may include lower alkyl substituents, particularly methyl and ethyl groups. In one embodiment such substituents are located at the 2 or 7 ring positions or at both of them. Further, other substituted and unsubstituted mono- and bicyclic aromatic moieties may be substituted at position Z for the phenolic moiety employed in making complex 232. For example, other phenolic, alkylphenolic, hydroxynaphthalenyl, alkyl-hydroxynaphthalenyl, 8-hydroxyquinolinyl, and alkyl- 8-hydroxyquinolinyl moieties can be used. Specific, non limiting examples of suitable moieties that can constitute moiety Z shown in FIG. 5 include: phenolic, methyl phenolic, dimethyl phenolic, trimethyl phenolic, ethyl phenolic, diethyl phenolic, triethyl phenolic, hydroxynaphthalenyl, methylhydroxynaphthalenyl, dimethylhydroxynaphthalenyl, trimethylhydroxynaphthalenyl, 8-hydroxyquinolinyl, methyl-8-hydroxyquinolinyl, dimethyl-8-hydroxyquino-linyl, and trimethyl-8-hydroxyquinolinyl.

Further, other aromatic compounds having electron-donating groups can be substituted for the basic 8-hydroxyquinoline structure shown in FIGS. 2, 3 and 5. The functionality of the 8-hydroxyquinoline molecules depends on the alignment of the electron-donating nitrogen and oxygen atoms in a suitable orientation to complex with the erbium atom. Other molecular platforms for chelating erbium atoms having similar functionalities can be designed.

Figure 6:
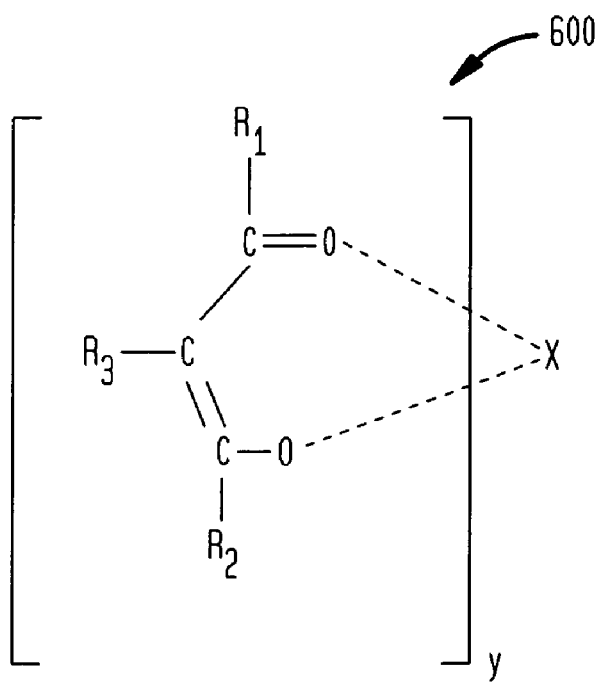

FIG. 6 shows an embodiment of an additional exemplary class of lanthanide atom-comprising guest molecules that can be used in accordance with the present invention. In the formula 600, each of $R_1$ and $R_2$ independently can be a hydrocarbon moiety, or a hydrocarbon moiety comprising an electron withdrawing group as detailed earlier. In one embodiment according to the present invention, one of $R_1$ and $R_2$ is a hydrocarbon moiety, and the other one of them is a hydrocarbon moiety comprising an electron withdrawing group. In a further embodiment according to the present invention, such electron withdrawing group is a linear or branched halogenated or perhalogenated alkyl group, such as, for example, a heptafluoropropyl or pentafluoroethyl group. In an additional embodiment according to the present invention, such hydrocarbon moiety is a linear or branched alkyl group, such as a methyl, ethyl, propyl, or tert-butyl group. $R_3$ is an electron withdrawing group, a lower alkyl group, or hydrogen. X is a selected lanthanide metal, coordinated with the two oxygen atoms as indicated by dotted lines. The oxygen atom covalently bound by a single carbon bond has lost a hydrogen ion. Y is equal to the valence of the selected lanthanide metal. For example, if the lanthanide is erbium having a valence of $3^+$, then Y equals 3. In one embodiment according to the present invention, $R_1$ is a heptafluoropropyl group, $R_2$ is a tert-butyl group, $R_3$ is hydrogen, and the lanthanide is erbium. The resulting guest molecule is erbium tris(6,6,7,7,8,8,8-heptafluoro-2,2-dimethyl-3,5-octanedionate). This guest molecule complex can also be referred to by the acronym, $Er(FOD)_3$, in which FOD denotes 6,6,7,7,8,8,8-heptafluoro-2,2-dimethyl-3,5-octanedionate. This guest molecule complex is commercially available from Alfa Aesar, 30 Bond Street, Ward Hill, Mass. 01835. Analogous guest molecules can be made by substituting other lanthanides. For example, praseodymium, ytterbium, neodymium and yttrium can be chelated to form $Pr(FOD)_3$, $Yb(FOD)_3$, $Nd(FOD)_3$, and $Y(FOD)_3$, respectively.

Figure 7:
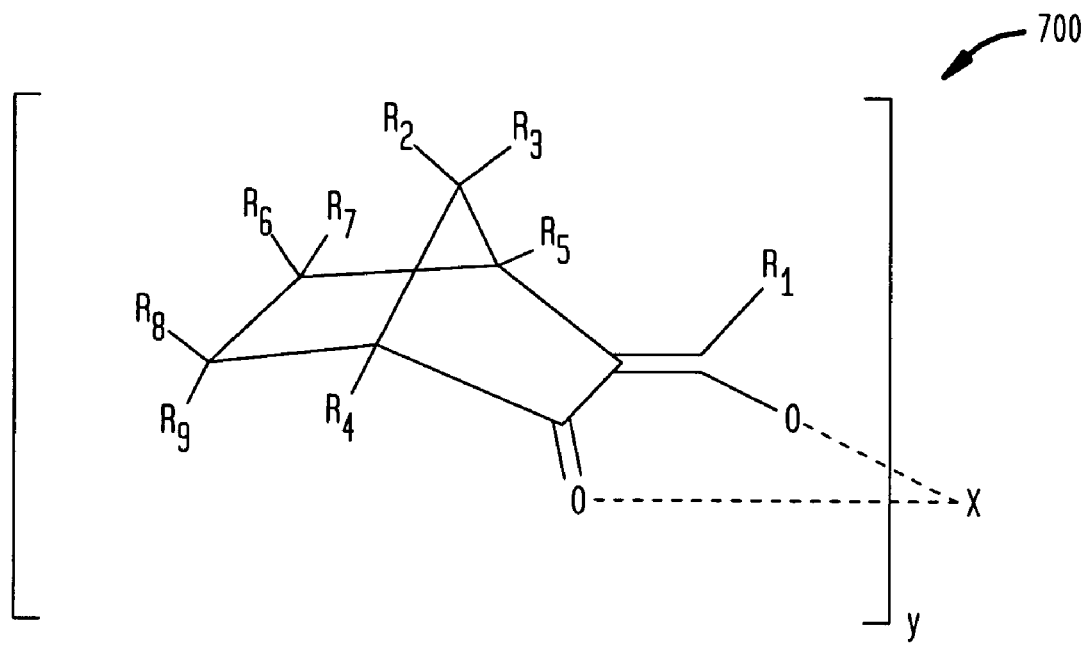
Figure 8:
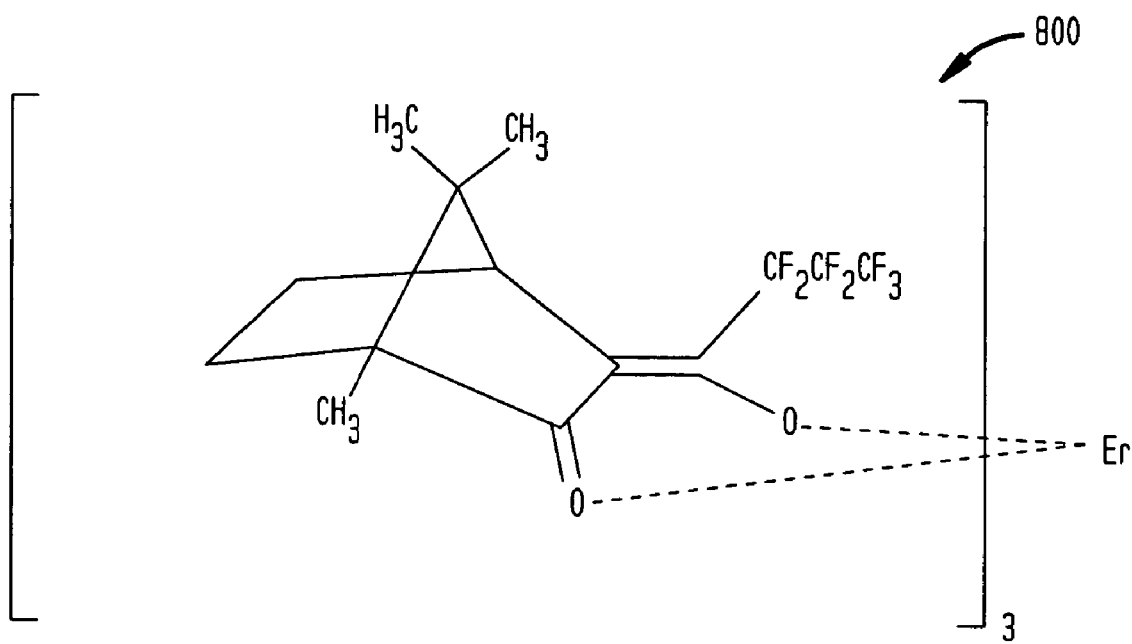
FIG. 8 shows an exemplary lanthanide atom-comprising guest molecule that can be used in accordance with the present invention.

FIG. 7 shows an embodiment of an additional exemplary class of lanthanide atom-comprising guest molecules that can be used in accordance with the present invention. In the formula 700, $R_1$ is a hydrocarbon moiety comprising an electron withdrawing group. Each of $R_2$, $R_3$, $R_4$, $R_5$, $R_6$, $R_7$, $R_8$ and $R_9$ is hydrogen or a lower alkyl group such as, for example, a methyl or ethyl group. X is a selected lanthanide metal, coordinated with the two oxygen atoms as indicated by dotted lines. The oxygen atom covalently bound by a single carbon bond has lost a hydrogen ion. Y is equal to the valence of the selected lanthanide metal. For example, if the lanthanide is erbium having a valence of $3^+$, then Y equals 3. In one embodiment according to the present invention, $R_1$ is a linear or branched halogenated or perhalogenated alkyl group, such as, for example, a heptafluoropropyl, pentafluoroethyl, or trifluoromethyl group, each of $R_2$, $R_3$, and $R_4$ is a methyl group, each of $R_5$, $R_6$, $R_7$, $R_8$ and $R_9$ is hydrogen, and the lanthanide is erbium. FIG. 8 shows a specific exemplary embodiment of a lanthanide atom-comprising guest molecule 800 that can be used in accordance with the present invention, in which $R_1$ as shown in FIG. 7 is a heptafluoropropyl group. The resulting guest molecule is erbium tris[3-(heptafluoropropylhydroxymethylene)-camphorate]. This guest molecule complex is commercially available from the Sigma-Aldrich Chemical Company, St. Louis, Mo. Analogous guest molecules can be made by substituting other lanthanides, such as, for example, praseodymium, ytterbium, neodymium and yttrium.

Those of ordinary skill in the art will readily design other monocyclic, bicyclic, and multicyclic aromatic compounds, optionally including heteroatoms and lower alkyl substituents, to provide further erbium atom-comprising guest molecules suitable for positioning and retention within the bridged polysilsesquioxane host matrices according to the present invention.

In a further embodiment according to the present invention, the above aromatic erbium atom-comprising guest molecules are supplemented by addition of erbium triisopropoxide, having the formula $Er-(OC_3H_7)_3$. Since this additional erbium is thus carried by alkoxy groups, it can be directly co-condensed into the bridged polysilsesquioxane host matrix itself. The aromatic erbium atom-comprising guest molecules together with the erbium directly condensed into the polysilsesquioxane host matrix provide a higher cumulative density of erbium doping. Further, the erbium directly condensed into the polysilsesquioxane host matrix helps direct the aromatic erbium atom-comprising guest molecules into chelated positions. Other erbium compounds, such as erbium triethoxide and erbium trimethoxide, as well as erbium oxide, can also be used.

In another embodiment according to the present invention, the above aromatic compounds are omitted and the sole erbium atom-comprising guest molecule is erbium triisopropoxide, having the formula $Er-(OC_3H_7)_3$. In yet a further embodiment according to the present invention, the sole erbium atom-comprising guest molecule is erbium oxide, having the formula $Er_2O_3$.

Referring again to FIG. 2, the bridged polysilsesquioxane host matrix is also subject to modification as desired. The polysilsesquioxane host matrix shown in FIG. 2 comprises four organic moieties 236, 238, 240 and 242 held together by polysilsesquioxane bonds formed at the four corners 222, 224, 226 and 228 of cell 200. Exemplary organic moiety 236 contains a linear chain of 14 carbon atoms that is interrupted only by the two urethane groups 244 and 245. Variations on this structure can include extending or shortening the carbon chain, introducing branched or unsaturated groups, and including cyclic or aromatic groups. Combinations of such modifications are included.

Shortening the carbon chain can reduce the available sites for binding of electron donating groups and electron withdrawing groups, and lengthening the carbon chain can increase such available sites. For example, exemplary propyl group 260 may be substituted by a straight- or branched-chain alkyl group of any desired length, with or without unsaturation.

Exemplary urethane group 245 may be substituted or supplemented by any suitable electron donating group, such as, for example, an amine group. The term amine is to be broadly construed, and includes, for example, urethanes and amides. Further, a suitable electron donating group may be bound to the carbon chain, such as —$NR_2$, —$NH_2$, —NRH, or —OR, in which R is a lower alkyl such as, for example, methyl or ethyl. In addition, phosphorus can be substituted for nitrogen.

Exemplary fluoroalkyl group 252 contains four difluoromethyl groups interposed between two methylene groups. This structure may be modified by addition or subtraction of any desired number of difluoro or methylene groups, by introduction of monofluoro groups, and by introduction of branching or unsaturation. Further, fluorine can be replaced in whole or part by other halogens such as chlorine, bromine and iodine. In addition, exemplary fluoroalkyl group 252 may be substituted or supplemented by any suitable electron withdrawing group bound to the carbon chain, such as, for example, a —CN (cyano) group or an —$SO_3H$ (sulfonic acid) group. Further, halogens can be incorporated in other straight- or branched-chain hydrocarbon moieties including, for example, alkyl, alkenyl and alkynyl substituents bound to the carbon chain, such as —$CF_3$.

In one embodiment according to the present invention, highly fluorinated organic compounds are employed to prepare bridged polysilsesquioxane host matrices. The active organic moieties in the resulting polysilsesquioxane host matrices generate strong repulsion of —Si—OH groups and thus strongly repel uncondensed —Si—OH groups away from the hydrophobic organic regions to molecular environments where they are closer together and thus can more readily condense. In addition, the structures of these bridged polysilsesquioxane host matrices create enlarged spaces suitable for containing larger chelated guest molecules.

Figure 9:
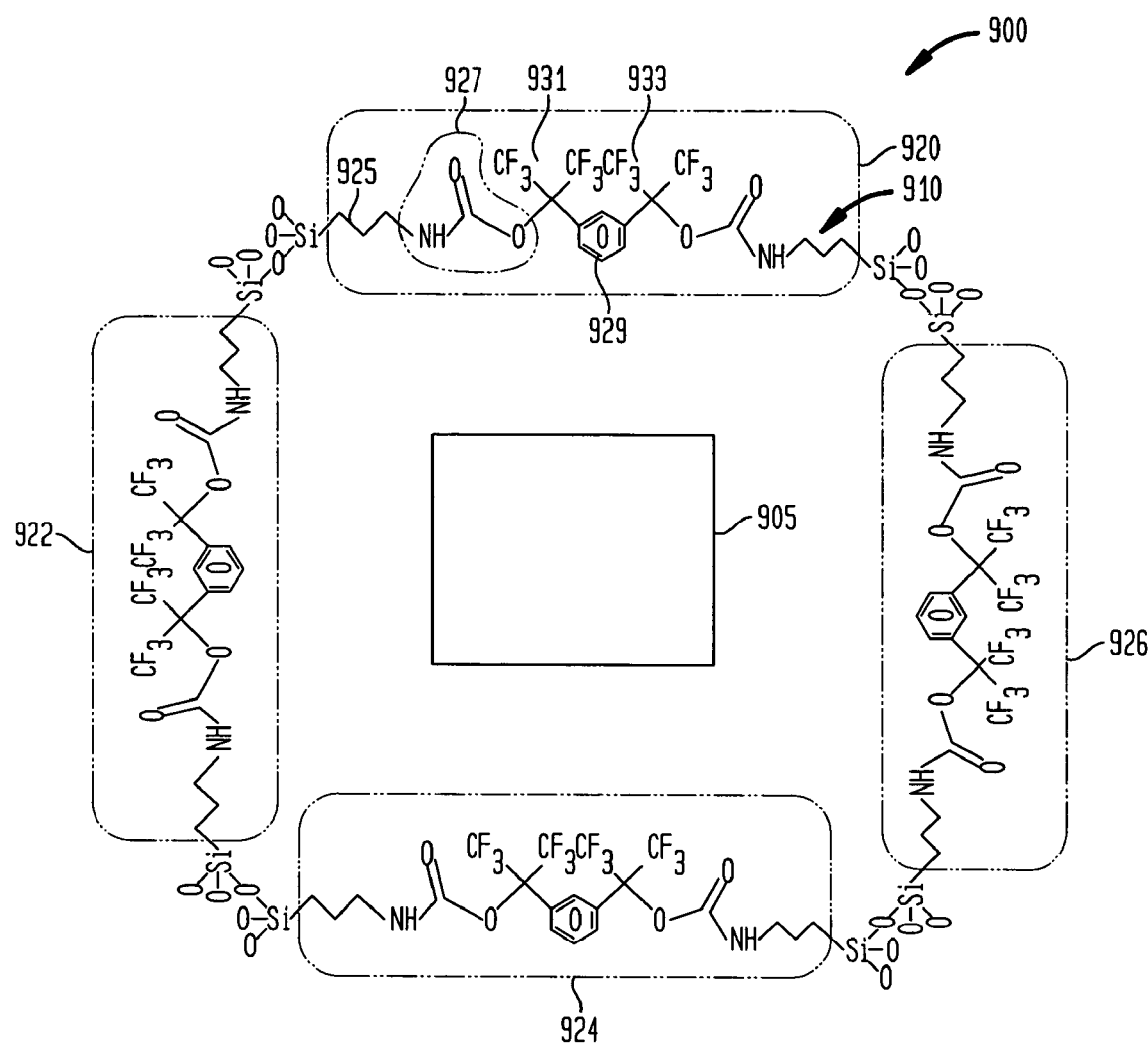
FIG. 9 shows an exemplary embodiment of a representative cell of the structure of another bridged polysilsesquioxane composition in accordance with the present invention.

FIG. 9 shows an exemplary embodiment of a representative cell 900 of the structure of a highly fluorinated bridged polysilsesquioxane composition in accordance with the present invention. The guest molecule is indicated at 905. The polysilsesquioxane host matrix 910 shown comprises four organic moieties 920, 922, 924 and 926. Exemplary organic moiety 920 comprises two propyl groups exemplified by propyl group 925. The organic moiety 920 comprises two urethane groups exemplified by urethane group 927. Further, the organic moiety 920 comprises a phenyl group 929 meta-bonded by two di(trifluoromethyl)methylene groups 931 and 933. This embodiment illustrates the feasibility of incorporating aromatic and trihalomethyl groups into the organic moieties of the bridged polysilsesquioxane host matrix.

Figure 10:
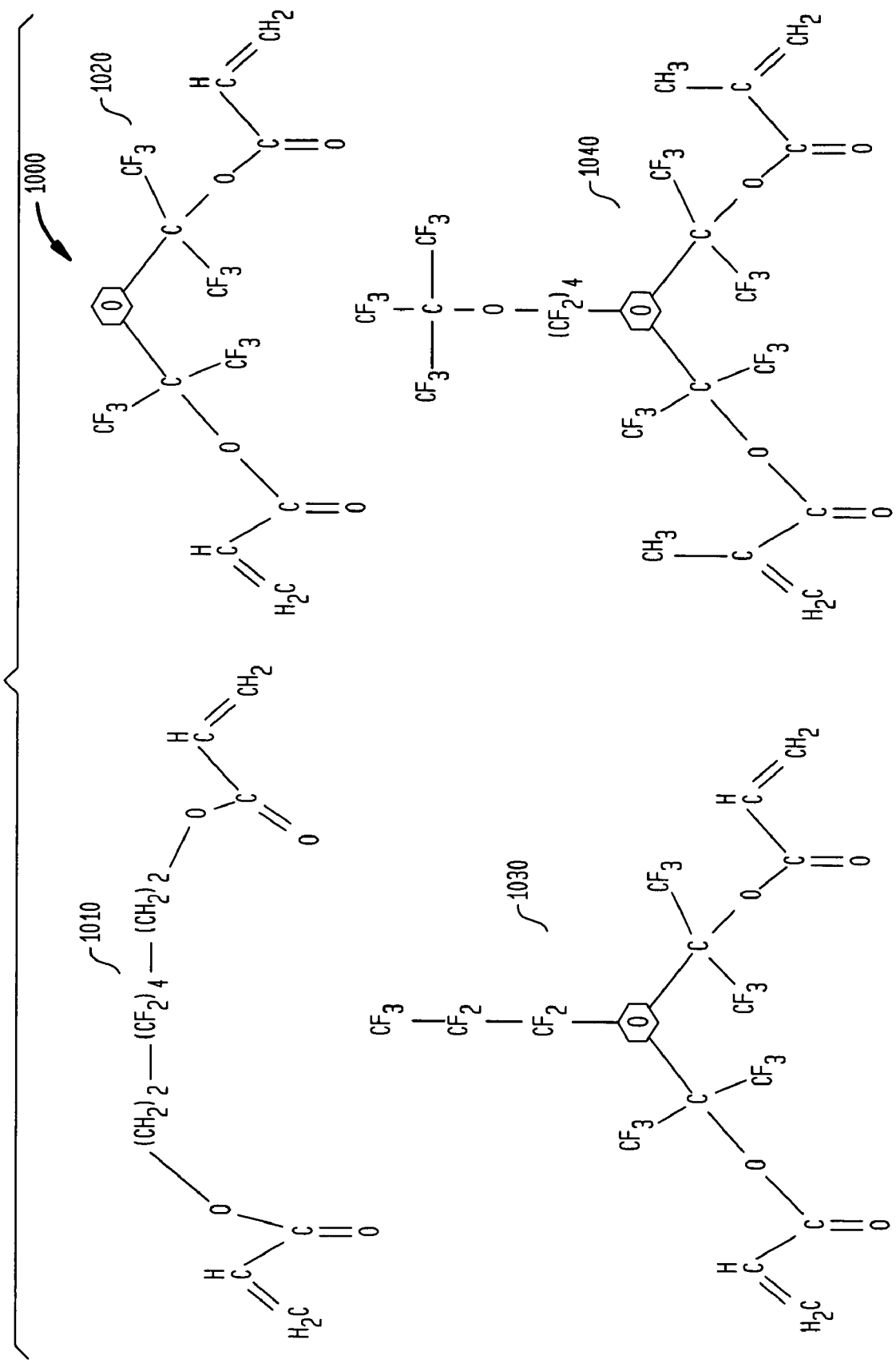
FIG. 10 shows an array of fluorine-containing organic compounds for producing organic moieties to be incorporated into bridged polysilsesquioxane compositions in accordance with the present invention.

Referring to FIG. 10, an array 1000 of exemplary fluorine-containing organic compounds for producing organic moieties are shown. Organic compounds 1010, 1020, 1030, and 1040 include 8, 12, 19 and 29 fluorine atoms, respectively. The fluorine content of these four organic compounds is 38.17%, 43.99%, 52.60% and 55.14% by weight, respectively.

The dielectric constant of a material is indirectly indicative of void space and thus efficiency of packing. The dielectric constant of air is 1. As the dielectric constant of a material decreases, its porosity increases. The dielectric constants of bridged polysilsesquioxane host matrices produced from organic compounds 1010, 1020, 1030 and 1040 are 2.41, 2.25, 2.21 and 2.07, respectively. Hence, as expected, as the size and complexity of these highly fluorinated organic compounds increases, so does the void space that they produce in a polysilsesquioxane gel matrix. This increased void space is due both to increased sizes of polysilsesquioxane cells, as well as to less efficient packing of cells together.

The compounds shown in FIG. 10 are commercially available from Lancaster Synthesis Inc, P.O. Box 1000, Windham, N.H. 03087. Those of ordinary skill in the art will readily design and employ variations of these chemical structures to produce other highly fluorinated bridged polysilsesquioxane gels having high void space. The active diene moieties can be replaced by other groups, such as alkoxides. In one embodiment according to the present invention, di(trialkoxysilyl) monomers comprising at least about 38% by weight of fluorine are provided. In another embodiment according to the present invention, di(trialkoxysilyl) monomers comprising at least eight fluorine atoms are provided. In a further embodiment according to the present invention, di(trialkoxysilyl) monomers comprising at least about 50% by weight of fluorine are provided. In an additional embodiment according to the present invention, di(trialkoxysilyl) monomers comprising at least nineteen fluorine atoms are provided. In addition, other halides such as chlorine, bromine and iodine can be used. Further, other electron withdrawing groups as discussed above can be used.

The discussion above has employed erbium as the exemplary lanthanide element to be complexed into the bridged polysilsesquioxane host matrix. However, any other lanthanide or lanthanide mixture can be substituted. In one embodiment according to the present invention, cerium, praseodymium, neodymium, promethium, samarium, europium, gadolinium, terbium, dysprosium, holmium, thulium, ytterbium, lutetium, yttrium, scandium, erbium, lanthanum, or a mixture is employed. In another embodiment according to the present invention, erbium, praseodymium, neodymium, or a mixture optionally including other co-dopants, is employed. Erbium, for example, fluoresces at about 980 nm and about 1540 nm and is useful for amplifying signals carried in the ranges of about 900-1000 nm and about 1500-1600 nm. Praseodymium fluoresces at about 1310 nm is useful for amplifying signals carried in the range of about 1260-1360 nm. The photoluminescent lifetimes of these emissions approach milliseconds, comparable with conventional lanthanide doped materials.

As earlier discussed, the present invention is not limited to production of polysilsesquioxanes, as silicon can be replaced in whole or part by other metallic elements such as aluminum, titanium, zirconium and germanium in any or all of the reagents employed. In this regard, silicon tetraethoxide (Si(OCH$_2$CH$_3$)$_4$), having four ethoxy ligands, can serve as a model for the polymerization of silsesquioxanes to produce a polysilsesquioxane composition. Accordingly, titanium tetraethoxide ($Ti(OCH_2CH_3)_4$), zirconium tetraethoxide ($Zr(OCH_2CH_3)_4$), germanium tetraethoxide ($Ge(OCH_2CH_3)_4$) and aluminum triethoxide ($Al(OCH_2CH_3)_3$) can serve as models for the polymerization of corresponding sesquioxanes to produce corresponding polysesquioxane compositions. The synthetic chemistry required to prepare the needed reagents and carry out the polymerizations follows from the relationships between these ethoxide models.

The exemplary erbium atom-comprising guest molecule 232 can be prepared from 8-hydroxyquinaldine, erbium-triisopropoxide, and phenol. These reagents are all commercially available from Sigma-Aldrich. Erbium triisopropoxide is also commercially available from Chemat Technology, 9036 Winnetka Avenue, Northridge, Calif. 91324. For example, in a first reaction carried out in the presence of ethanol and heat, two mole equivalents of 8-hydroxyquinaldine and one mole equivalent of erbium triisopropoxide are allowed to react, yielding a complex of erbium monoisopropoxide with two dehydrogenated 8-hydroxyquinaldine molecules, and propanol as a byproduct. This complex is then combined with a stoichiometrically equal amount of phenol while heating under reflux conditions, yielding the erbium atom-comprising guest molecule 232, again with propanol as a byproduct. The other exemplary erbium atom-comprising guest molecules 310-340 shown in FIG. 3 can be synthesized in an analogous manner. In order to synthesize guest molecule 310, meta-methyl phenol is substituted for phenol. In order to synthesize guest molecule 320, 2,4,6-trimethylphenol is substituted for phenol. In order to synthesize guest molecule 330, hydroxynaphthalene is substituted for phenol. In order to synthesize guest molecule 340, 8-quinolinol is substituted for 8-hydroxyquinaldine and for phenol. All of the reagents necessary for making guest molecules 310-340 also are commercially available from Sigma-Aldrich. Analogous compounds based on other lanthanides can be made by substituting the appropriate lanthanide isopropoxide for erbium triisopropoxide. Praseodymium isopropoxide and neodymium isopropoxide are commercially available from Cardinal Industries Inc., 4601 W. Woolworth Ave., Milwaukee, Wis. 53218.

Preparation of the bridged polysilsesquioxane host matrices is carried out in the presence of the selected guest molecules, which become distributed in and chelated to the resulting polysesquioxane cells as exemplified by cells 10 and 20 shown in FIG. 1. First, the appropriate monomers for sol-gel synthesis of the host matrix need to be prepared. Sol-gel synthesis is generally carried out by condensation of Si—OH bonds within silsesquioxane monomers to produce —Si—O—Si— bonds, and water as a byproduct. These reactions can typically be carried out at a relatively low temperature, such as room temperature, making the sol-gel process desirable for the production of polymeric systems having intact organic substituents. Given the reactivity of —Si—OH groups, storage stability of the monomers to be polymerized can be improved, and potentially explosive exothermic reactions can be avoided, by providing the monomers with corresponding ethoxy groups. Alternatively, methoxy groups or propoxy groups can be used, but the former may allow reactions to proceed too rapidly and the latter may cause reactions to proceed too slowly.

Thorough mixing of the reagents for production of the bridged polysilsesquioxane host matrix together with the selected guest molecule compound is important to avoid phase separations. Otherwise, discrete guest molecule domains may result. In addition, inadequate reagent mixing may cause the proportion of uncondensed —Si—OH groups to increase.

Figure 11:
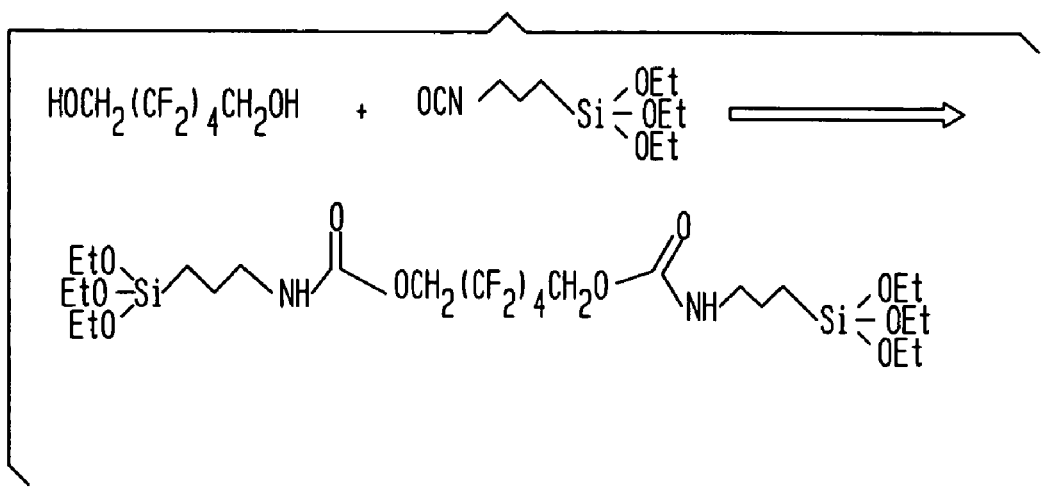
FIGS. 11-13 show synthesis reactions for producing organic-bridged di(triethoxysilyl) precursor monomers for use in making bridged polysilsesquioxane compositions in accordance with the present invention.

Referring to FIG. 2, monomers containing the exemplary organic moiety 236 and having —$Si(OC_2H_5)_3$ groups at both ends are needed to synthesize exemplary bridged polysilsesquioxane host matrix 229. Referring to FIG. 11, such monomers can be synthesized by reaction of 2,2,3,3,4,4,5,5 octafluoro-1,6-hexanediol with (3-isocyanatopropyl)triethoxysilane. Both of these reagents are commercially available from Sigma-Aldrich and from Lancaster Synthesis. The reagents are thoroughly purified, for example by multi-stage vacuum distillation, to a purity exceeding 99% by weight. A small amount of 2,2,3,3,4,4,5,5 octafluoro-1,6-hexanediol is placed inside a suitable flask such as a round bottom flask under an anhydrous atmosphere. Next, a commensurate amount of (3-isocyanatopropyl)triethoxysilane is dropwise added to the flask. A suitable solvent such as toluene can be added to aid mixing of the two compounds. The reaction, as shown in FIG. 11, yields 2,2,3,3,4,4,5,5-octafluoro-1,6-hexanediol-bis(3-triethoxysilyl)propylcarbamate. This reaction is highly exothermic and preferably is allowed to take place at room temperature or, for example, about 25° C. without any catalyst. The reaction is sluggish and a reaction time over a week may be necessary for its completion. Reaction progress can be monitored, for example, by gas chromatography (GC), mass spectroscopy, or NMR. The carbamate product should be refrigerated to prevent premature hydrolysis of the ethoxysilyl groups and resulting polymerization.

The bridged polysilsesquioxane host matrix 229 shown in FIG. 2 can then be produced by condensation of 2,2,3,3,4,4,5,5-octafluoro-1,6-hexanediol-bis(3-triethoxysilyl)propyl carbamate in the presence of a selected guest molecule. Desirably, tetraethylorthosilicate (TEOS), commercially available from Sigma-Aldrich, is co-condensed with the carbamate. TEOS is a much smaller molecule than the carbamate, and thus can aid in furthering the completion of the condensation reaction and in conversion of —SiOH groups to —Si—O—Si— bonds. TEOS will tend to agglomerate into phase separated regions rather than be intercalated into the structure of individual silsesquioxane host matrix cells. The carbamate monomer, optionally including TEOS, is mixed into a suitable solvent such as ethanol or tetrahydrofuran (THF) to yield, for example, a 0.4 molar solution of the monomer, with addition of a small proportion, for example about 1 to about 5% by atomic weight equivalent, preferably about 1 to about 1.5% by atomic weight equivalent, of an erbium atom-comprising guest molecule. Relatively low proportions of the erbium atom-comprising guest molecule are preferred in order to avoid the self quenching effect. The THF, if used, should be thoroughly dried by distillation with stirring for several days using potassium as a drying agent. The condensation reaction can be conventionally catalyzed either by an aqueous acid or base such as, for example, hydrochloric acid or sodium hydroxide, with a substantial excess, for example about a six-fold stoichiometric excess, of water. The resultant sols are then left to gel in glass vials at a slightly elevated temperature, for example about 35° C. After gelation, the bridged polysilsesquioxanes are annealed at successively increasing temperatures ranging up to, for example, 200° C., preferably up to about 125° C., over two weeks. This annealing process causes the condensation of further remaining —Si—OH groups, thus reducing their undesired absorption of fluorescent emissions. The sol-gel process successively produces sols, aerogels, and zerogels of increasing density and rigidity.

Figure 12:
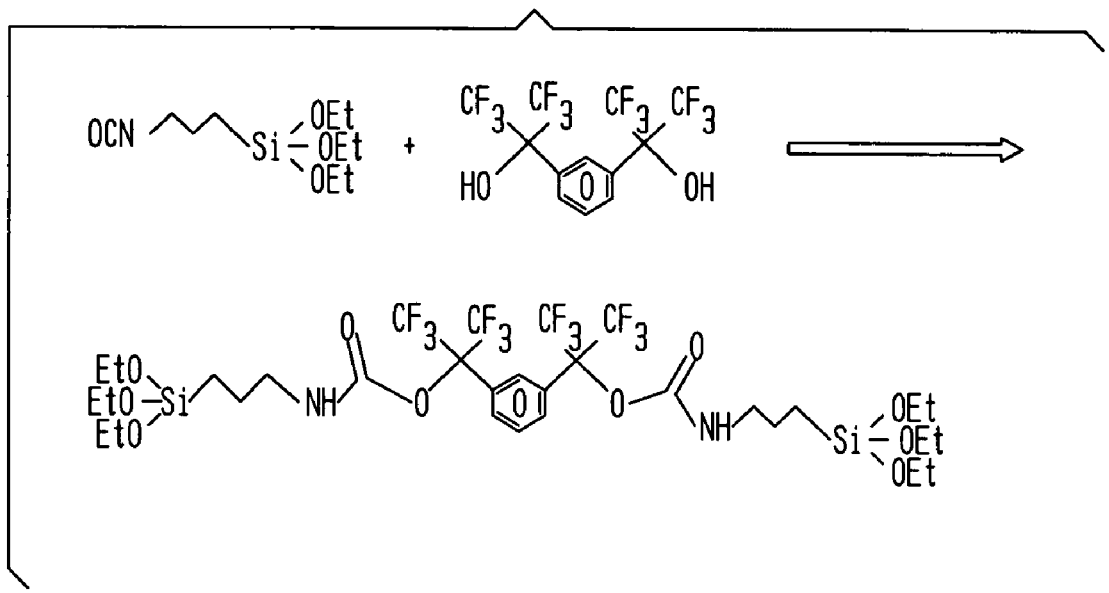

Referring to FIG. 9, monomers containing the exemplary organic moiety 920 and having —$Si(OC_2H_5)_3$ groups at both ends are needed to synthesize exemplary bridged polysilsesquioxane host matrix 910. Referring to FIG. 12, in order to prepare such monomers, α,α,α,α-tetrakis(trifluoromethyl)-1,-benzene-dimethanol and (3-isocyanatopropyl)triethoxysilane can be used. The former compound is commercially available from Lancaster Synthesis, and the latter compound is commercially available from Sigma-Aldrich. The reagents are purified in the same manner as discussed above. A small amount of α,α,α,α-tetrakis(trifluoromethyl)-1,3-benzenedimethanol is placed inside a suitable flask under an anhydrous atmosphere. Next, a commensurate amount of (3-isocyanatopropyl)-triethoxysilane is dropwise added to the flask. A suitable solvent such as toluene can be added to aid mixing of the two compounds. The reaction yields the di-triethoxysilyl compound shown in FIG. 12. This reaction is highly exothermic and preferably is allowed to take place at room temperature or, for example, about 25° C. without any catalyst. As above, the reaction is sluggish and a long reaction time, for example as long as a week, may be necessary for its completion. The product should be refrigerated to prevent premature hydrolysis of the ethoxysilyl groups and resulting polymerization. The bridged polysilsesquioxane host matrix 910 shown in FIG. 9 can then be produced in the same manner as discussed above regarding production of polysilsesquioxane host matrix 229, by condensation of the di-triethoxysilyl compound shown in FIG. 12 in the presence of a selected guest molecule.

Figure 13:
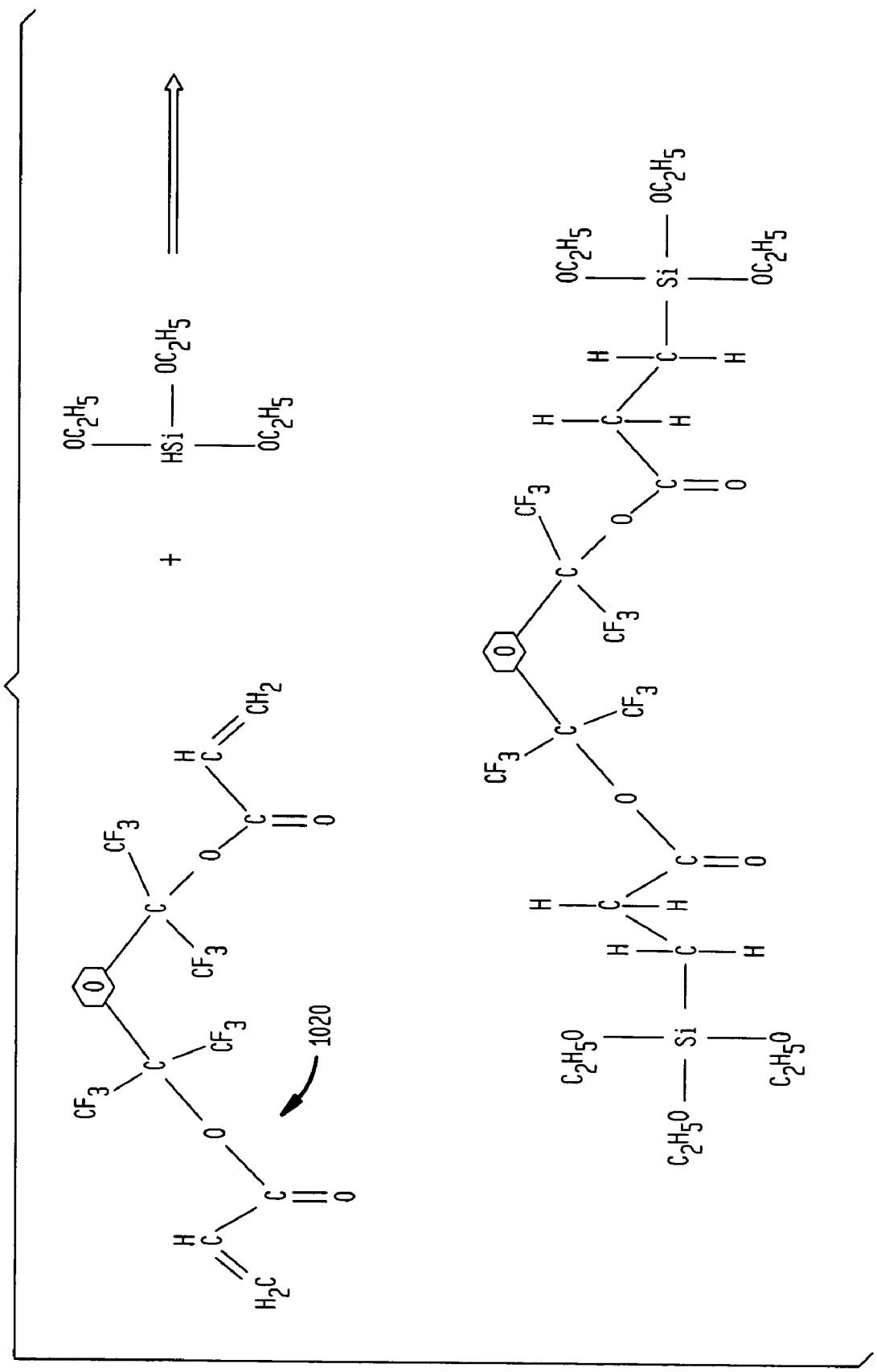

Referring to FIG. 10, monomers containing the active moieties of exemplary organic compound 1020 and having —Si(OC$_2$H$_5$)$_3$ groups at both ends are needed to synthesize a corresponding bridged polysilsesquioxane host matrix. In one embodiment according to the present invention, alkyldiene compound 1020 is commercially obtained and hydrosilylated with triethoxysilane. Chloroplatinic acid, having the formula H$_2$PtCl$_6$ and known also as Speier's catalyst, serves to catalyze this reaction. Isopropanol is employed as a solvent. This reaction is shown in FIG. 13. For example, one molar equivalent of alkyldiene compound 1020 and two molar equivalents of triethoxysilane, a catalytic amount of chloroplatinic acid and isopropanol as a solvent are mixed in a round bottom flask. A magnetic stirrer is used to thoroughly mix the reagents over 5-24 hours. GC analysis is employed to monitor the degree of completion of the reaction. The product is then refrigerated.

In one embodiment according to the present invention, semiconductor quantum-dot particles of a suitable composition and having a size range between about 15 Å and about 100 Å are added to the reagents for producing the bridged polysilsesquioxane host matrix. Semiconductor quantum-dot particles become distributed within the cells of the polysilsesquioxane host matrix, for example in the vicinity of the guest molecule. Suitable semiconductor quantum-dot compositions include, for example, cadmium selenide, cadmium sulfide, cadmium oxide, zinc selenide, zinc sulfide, and zinc oxide. These compounds are commercially available from ESPI, 1050 Benson Way, Ashland, Oreg. 97520. They are typically supplied in a dispersed form with a suitable binder, such as 3-aminopropyltriethoxysilane. Nanoparticles of these semiconductor quantum-dot compounds can be conventionally produced. Introduction of semiconductor quantum-dot nanoparticles results in an increasing number of phonon emissions having a lowered level of phonon energy. This lowered phonon energy results in lowered vibration energy in the Er$^{3+}$ microenvironment, and enhances the lanthanide fluorescence. Semiconductor quantum-dot nanoparticles are particularly effective in the solid-state environment of the polysilsesquioxane compositions according to the present invention, as they are retained in effective positions in the vicinity of the lanthanide atoms within the guest molecules. Cadmium selenide produced the strongest enhancement of fluorescent emissions in the systems tested. The phonon energy of cadmium selenide particles in a nanometer size range is 200 cm$^{-1}$.

In another embodiment according to the present invention, further dopants may be added to the reagents for producing the bridged polysilsesquioxane host matrix and the guest molecule prior to polymerization in order to tune the wavelength range of the fluorescent emissions. For example, yttrium, ytterbium, germanium or aluminum compounds may be added as co-dopants for this purpose. In one embodiment according to the present invention, yttrium oxide, ytterbium oxide, germanium oxide, aluminum oxide, or a mixture is used. In another embodiment according to the present invention, yttrium, ytterbium, germanium, aluminum or a mixture are chelated in the same guest molecule as chosen for chelation of the chosen lanthanide element, or in one of the other guest molecules disclosed herein. In this manner, the selected co-dopant is dispersed within the cells of the polysilsesquioxane in the same manner as is the lanthanide, potentially serving to provide more precise control over the uniformity of distribution of both the lanthanide and co-dopant in the bridged polysilsesquioxane host matrix. Particles of such compounds become distributed within the cells of the polysilsesquioxane host matrix, for example in the vicinity of the guest molecule.

Bridged polysesquioxane host matrices with incorporated guest molecules in accordance with the present invention can be optically analyzed, for example by acquisition of photoluminescent spectra using the 488 nm line of an argon ion laser at a power density of about 0.5 to about 5 watts per square centimeter.

The polysesquioxane host matrices according to the present invention are characterized by substantial reductions in uncondensed —Si—OH groups as compared with bridged polysesquioxane host matrices not incorporating electron withdrawing groups as discussed above. In one embodiment according to the present invention, at least about 81% of all reactive —Si—OH moieties are condensed into —Si—O—Si— bonds. In another embodiment according to the present invention, at least about 85% of all reactive —Si—OH moieties are condensed into —Si—O—Si— bonds. The proportion of condensed —Si—OH groups can be determined from the proportion of residual ethoxysilyl groups in the product. Infrared spectroscopy, Raman spectroscopy, and solid state NMR spectroscopy are suitable for this purpose. Concerning NMR spectroscopy, $^{29}$Si NMR identifies the —Si—O—Si— linkage and $^{13}$C NMR identifies residual ethoxysilyl groups. The bridged polysesquioxane host matrices and incorporated guest molecules in accordance with the present invention have a substantially uniform distribution of organic and inorganic moieties at the molecular level. Hence, these materials are substantially free of light scattering and phase separation problems.

The bridged polysesquioxane host matrices according to the present invention offer high temperature stability. In one embodiment according to the present invention, these matrices are chemically stable up to about 250° C. Thermal stability can be measured, for example, using thermogravimetry. A Rheometric Scientific Inc. thermogravimeter model no. PL-STA is suitable for this purpose. In order to carry out this thermal stability testing, a sample of a bridged polysesquioxane host matrix is heated under a nitrogen atmosphere using, for example, a heating rate of 10° C. per minute.

EXAMPLE 1

Preparation of the di-triethoxysilyl Compound Shown in FIG. 11

Several grams each of 2,2,3,3,4,4,5,5 octafluoro-1,6-hexanediol and (3-isocyanatopropyl)triethoxysilane were thoroughly purified by multi-stage vacuum distillation to a purity exceeding 99% by weight. About 1 g or 3.8 millimoles (mmol) of 2,2,3,3,4,4,5,5 octafluoro-1,6-hexanediol was placed inside a round bottom flask with toluene as a solvent. About 1.9 g or 4.3 mmol of (3-isocyanatopropyl)triethoxysilane was dropwise added to the flask. The reaction was allowed to take place over seven days at about 25° C. without any catalyst. The product, 2,2,3,3,4,4,5,5-octafluoro-1,6-hexanediol-bis(3-triethoxysilyl)propylcarbamate, was analyzed and found to be 98.6% pure, then refrigerated.

EXAMPLE 2

Production of Bridged Polysilsesquioxane Host Matrix 229 Shown in FIG. 2

The polysilsesquioxane host matrix 229 shown in FIG. 2 is produced by condensation of 2,2,3,3,4,4,5,5-octafluoro-1,6-hexanediol-bis(3-triethoxysilyl)propyl carbamate in the presence of selected exemplary erbium atom-comprising guest molecule 232. TEOS is co-condensed with the carbamate. THF is thoroughly dried by distillation with stirring for several days using potassium as a drying agent. The carbamate monomer in about a 0.4 molar concentration and a relatively small proportional amount of TEOS are then mixed into THF with addition of 5% by weight equivalent of erbium atom-comprising guest molecule 232. The condensation is catalyzed by 7.5 molar % hydrochloric acid or sodium hydroxide, with about a six-fold stoichiometric excess of water. The resultant sols are then left to gel in glass vials at approximately 35° C. After gelation, the bridged polysilsesquioxanes are annealed at successively increasing temperatures ranging up to about 125° C. over two weeks. The degree of conversion of ethoxysilyl groups to —Si—O—Si— linkages in the polysilsesquioxane is about 91.1% by weight.

EXAMPLE 3

Preparation of the Di-triethoxysilyl Compound Shown in FIG. 12

Referring to FIG. 9, monomers containing the exemplary organic moiety 920 and having —Si(OC$_2$H$_5$)$_3$ groups at both ends are needed to synthesize a corresponding bridged polysilsesquioxane host matrix. Referring to FIG. 12, in order to prepare such monomers, α,α,α,α-tetrakis(trifluoromethyl)-1,3-benzene-dimethanol and (3-isocyanatopropyl)triethoxysilane can be used. The former compound is commercially available from Lancaster Synthesis, and the latter compound is commercially available from Sigma-Aldrich. The reagents are purified in the same manner as in Example 1. About 1 g or 2.43 mmol of α,α,α,α-tetrakis(trifluoromethyl)-1,3-benzene-dimethanol is placed inside a round bottom flask. Next, about 2.1 g or 4.86 mmol of (3-isocyanatopropyl)triethoxysilane is dropwise added to the flask. Toluene is added to aid mixing of the two compounds. The reaction yields the di-triethoxysilyl compound shown in FIG. 12. This reaction is highly exothermic and preferably is allowed to take place at room temperature or about 25° C. without any catalyst. As above, the reaction is sluggish and a long reaction time, for example as long as seven days, may be necessary for its completion. The product is refrigerated to prevent premature hydrolysis of the ethoxysilyl groups and resulting polymerization.

EXAMPLE 4

Comparative Study

Figure 14:
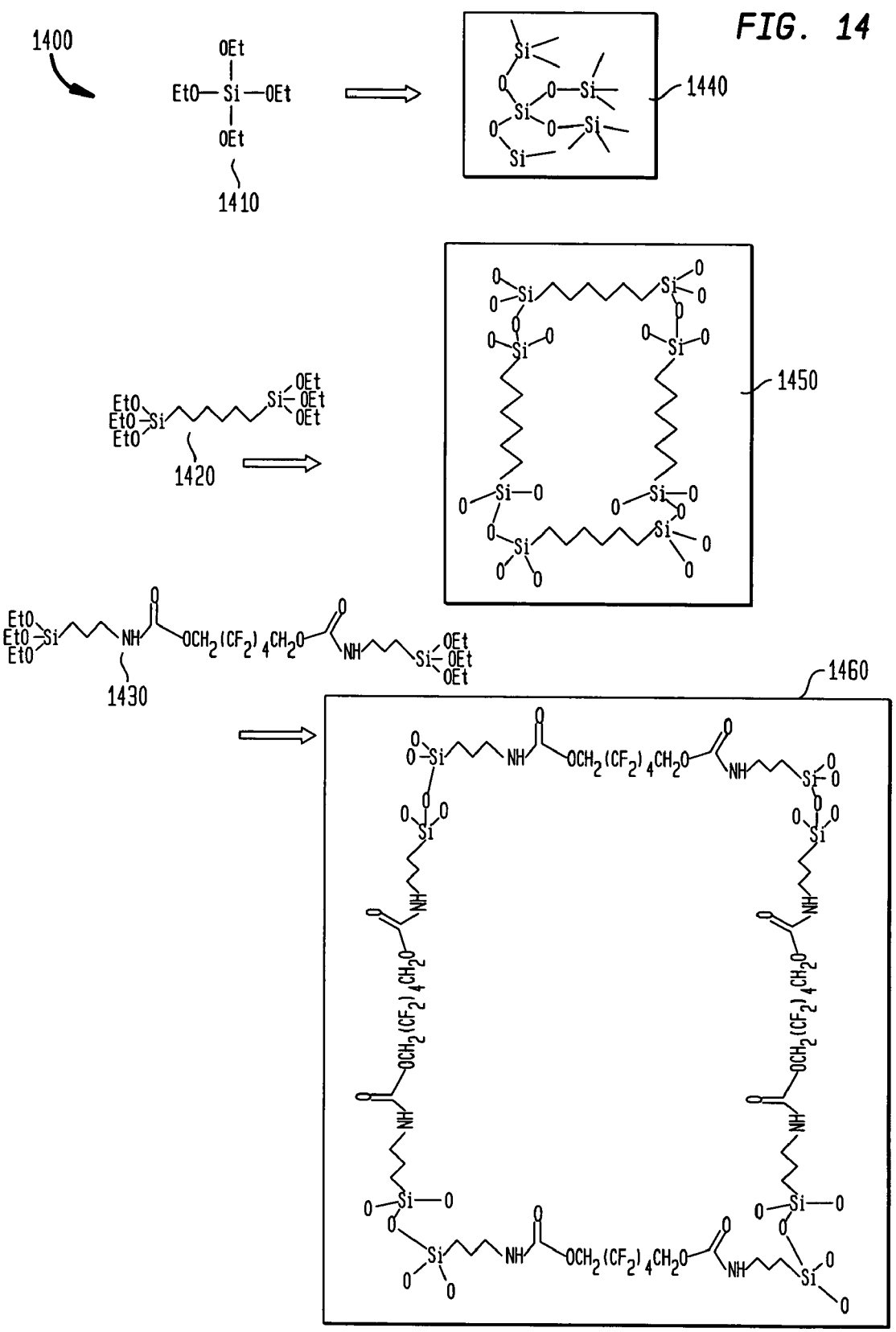
FIG. 14 shows an array of reactions for making bridged polysilsesquioxane compositions employed in a comparative study presented in Example 4.

In order to demonstrate advantageous features of the bridged polysilsesquioxane host matrices with chelated guest molecules according to the present invention, a comparative study of three different host matrices was carried out, each using a standardized proportion of erbium triisopropoxide as the guest molecule. FIG. 14 shows, together in a series 1400 of reaction schemes, the reagents used, and the resulting host matrices. The three reagents used, as shown in FIG. 14, were TEOS (1410), bis(triethoxysilyl)hexane (1420), and 2,2,3,3,4,4,5,5-octafluoro-1,6-hexanediol-bis(3-triethoxysilyl)propyl carbamate (1430), respectively. Representative cells of the resulting matrices are shown at 1440, 1450 and 1460, respectively. The host matrix 1460 shown in FIG. 14 was produced as reported in Examples 1 and 2.

The host matrix 1440 shown in FIG. 14 was produced by condensation of TEOS in the presence of erbium isopropoxide. TEOS obtained from Sigma-Aldrich was vacuum distilled to a purity in excess of 99%. THF was thoroughly dried by distillation with stirring for several days using potassium as a drying agent. TEOS was then mixed, to form about a 0.4 molar solution, into THF with addition of 5% by weight equivalent of erbium isopropoxide. The condensation was catalyzed, using a stoichiometric excess of water and the resultant sol was left to gel in a glass vial. After gelation, the matrix was annealed at successively increasing temperatures ranging up to about 125° C. over two weeks.

The host matrix 1450 shown in FIG. 14 was produced by condensation of bis(triethoxysilyl)hexane in the presence of erbium isopropoxide. In order to produce bis(triethoxysilyl)hexane, about 12.3 g or 0.15 mole of 1,5-hexadiene, about 54.1 g or 0.33 mole of triethoxysilane, and a catalytic amount of chloroplatinic acid in isopropanol were mixed in a round bottom flask. Mixing was aided by a magnetic stirrer. The mixture was kept in the reaction flask for about 5-24 hours with stirring until the appearance of the mixture changed from transparent to brown. Gas chromatographic analysis was employed to monitor the progress of the reaction. Mass spectroscopic analysis of the final product indicated a molecular weight of 411.2598, consistent with the calculated molar weight of C$_{18}$H$_{42}$Si$_2$+H. THF was thoroughly dried by distillation with stirring for several days using potassium as a drying agent. Bis(triethoxysilyl)hexane was then mixed, to form about a 0.4 molar solution, into THF with addition of 5% by weight equivalent of erbium isopropoxide. The condensation was catalyzed, using a stoichiometric excess of water and the resultant sol was left to gel in a glass vial. After gelation, the matrix was annealed at successively increasing temperatures ranging up to about 125° C. over two weeks.

After the sol-gel polymerizations were completed, the chemical compositions and degree of condensation of ethoxysilyl groups for the three gels were determined by spectroscopic techniques. The proportion of residual ethoxysilyl groups in these materials is indicative of the degree of hydrolysis. The methodologies used to characterize the polymers in this study included $^{13}$C and $^{29}$Si solid state NMR. The $^{13}$C NMR analysis was carried out to identify residual ethoxysilyl groups and the $^{29}$Si NMR analysis was carried out to identify formation of the —Si—O—Si— linkages. These solid state NMR analyses were carried out using a Varian Unity 400 solid state NMR spectrometer. Single pulse magic angle spinning (SP/MAS) NMR techniques were used for the characterization of the polymers, and a spin rate of 4000 hertz was employed. A line fitting routine was used in the analysis of the $^{29}$Si NMR resonances in each spectrum to establish the hydrolysis ratio of the subject siloxane structures. Silicon chemical shifts were referenced to an external sample of polysilane at 30.789 parts per million. A 7.5 millimeter Chemag probe with a teflon cap was used. Cross-polarized magic angle spinning (CP/MAS) NMR can also be used, with a pulse delay time of, for example, 3 milliseconds.

Figure 15:
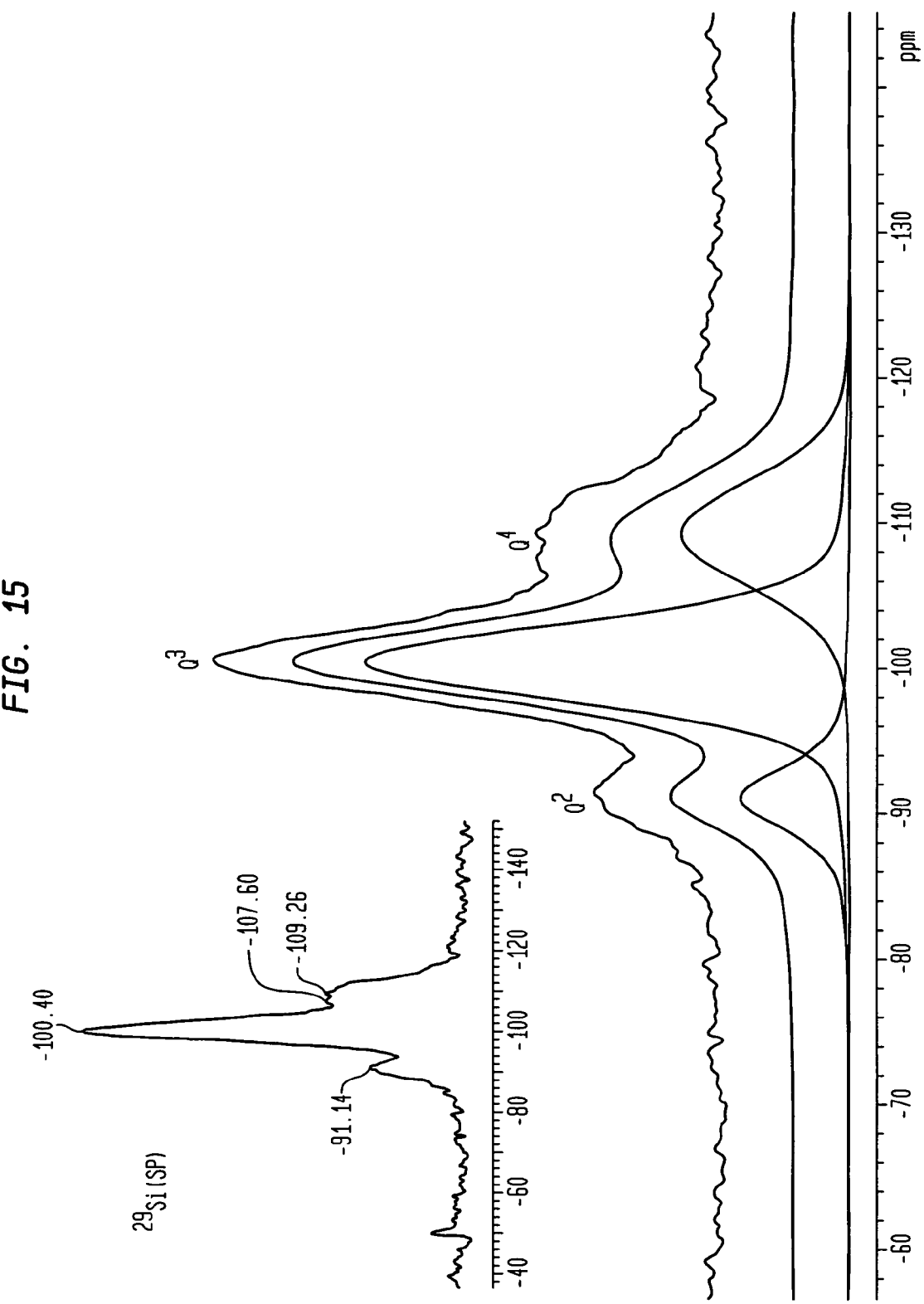
FIGS. 15-17 show graphed solid state nuclear magnetic resonance spectra in connection with Example 4.
Figure 16:
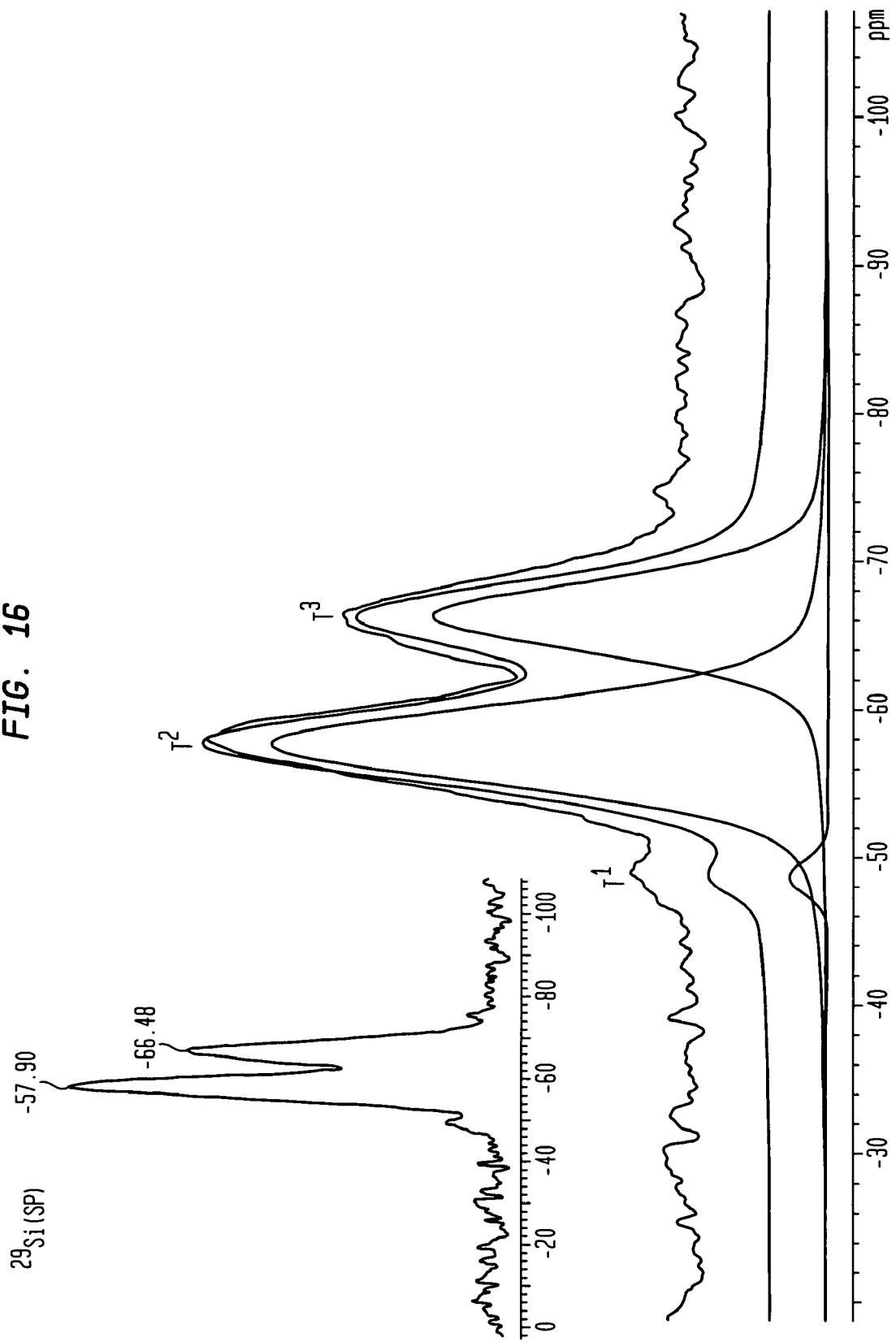
Figure 17:
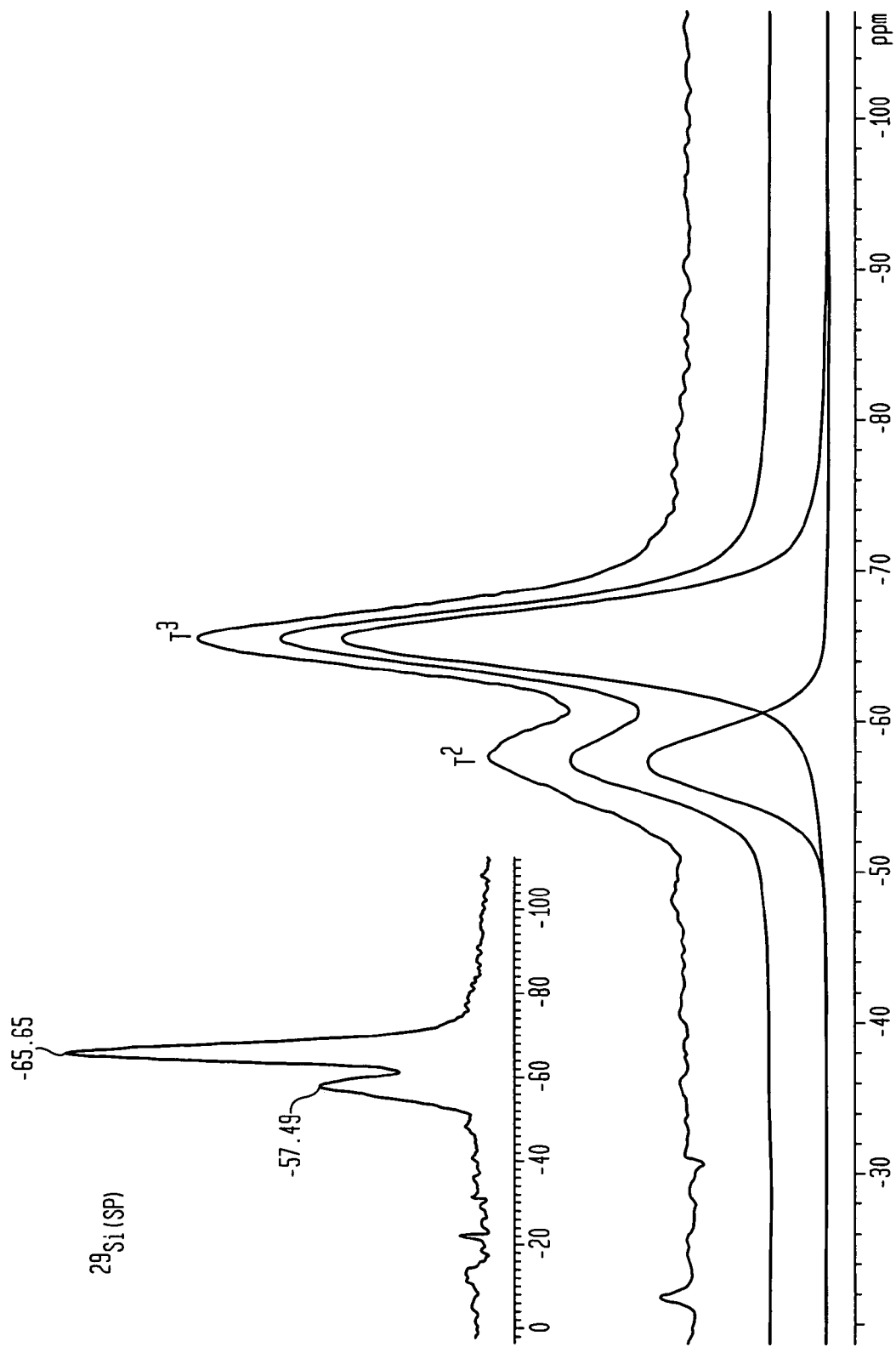

FIGS. 15, 16 and 17 show $^{29}$Si SP/MAS solid state NMR spectra relating to host matrices 1440, 1450 and 1460, respectively. The $^{13}$C NMR data confirmed the $^{29}$Si NMR results, but are not shown. Referring to FIG. 15, the $^{29}$Si solid state NMR spectrum relating to TEOS matrix 1440 shows three peaks, which correspond to $Q^2$, $Q^3$ and $Q^4$. The degree of conversion of ethoxysilyl groups to —Si—O—Si— linkages was about 78.8% by weight. Referring to FIG. 16, the $^{29}$Si solid state NMR spectrum relating to bis(triethoxysilyl)hexane shows three peaks, which correspond to $T^1$, $T^2$ and $T^3$. The degree of conversion of ethoxysilyl groups to —Si—O—Si— linkages was about 79.1% by weight. Referring to FIG. 17, the $^{29}$Si solid state NMR spectrum relating to 2,2,3,3,4,4,5,5-octafluoro-1,6-hexanediol-bis(3-triethoxysilyl)propyl carbamate shows only two peaks, which correspond to $T^2$ and $T^3$. The $T^1$ peak is not observed in this fluorinated system, and the $T^3$ peak intensity is greater than the $T^2$ intensity, contrary to the results in FIG. 16. The degree of conversion of ethoxysilyl groups to —Si—O—Si— linkages was about 91.1% by weight. Hence, ethoxysilyl conversion obtained with host matrix 1460 was dramatically increased as compared with host matrices 1440 and 1450.

Figure 18:
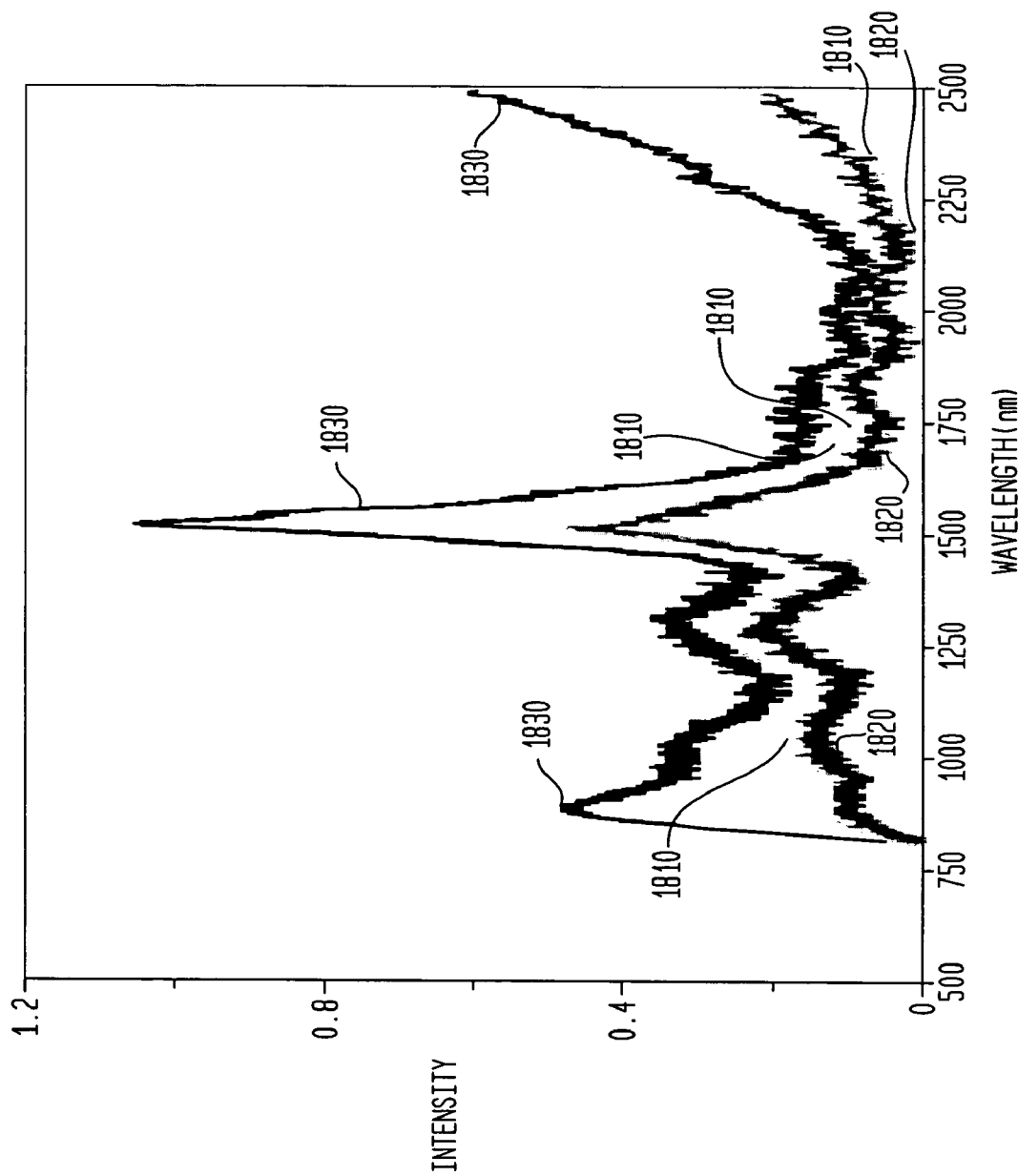
FIG. 18 shows graphed fluorescent intensity versus fluorescent wavelength for the three matrix systems compared in connection with Example 4.

Fluorescent spectroscopy of host matrices 1440-1460 was carried out by using an argon ion laser at 488 nm. Power densities of 1.5 and 3 watts per square centimeter were employed. FIG. 18 plots fluorescent intensity in a.u. on the vertical axis and fluorescent wavelength in nm on the horizontal axis. Curves 1810, 1820 and 1830 correspond to matrices 1440, 1450 and 1460, respectively. Since curves 1810 and 1820 closely overlap, curve 1810 is shown in gray and curve 1820 is shown in black. As shown, the Er3+ fluorescence intensity for fluorinated matrix 1460 was increased significantly more than for matrices 1440 and 1450. This higher fluorescence is attributable to the lower phonon energy in the matrix 1460 as well as the very homogeneous dispersion of erbium ions.

Figure 19:
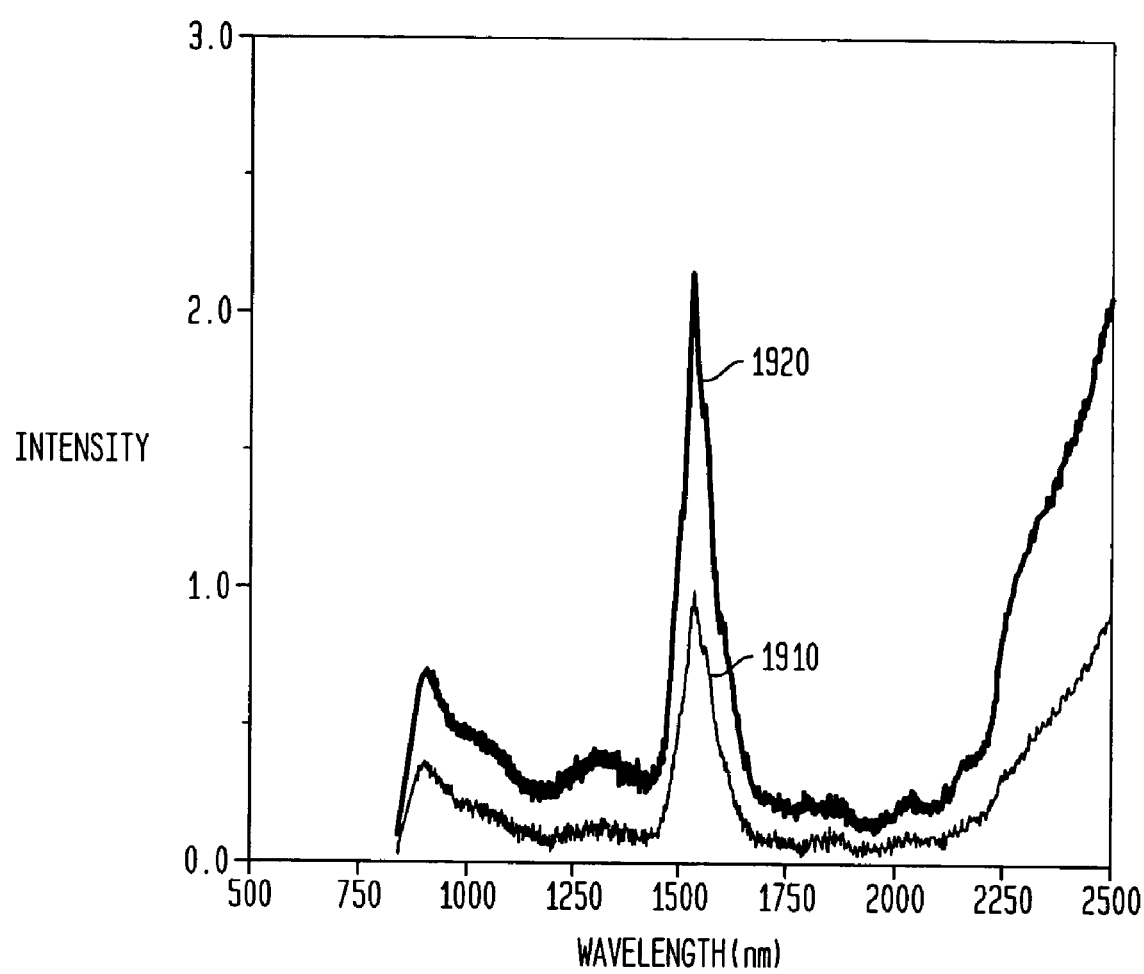
FIG. 19 shows graphed fluorescent intensity versus fluorescent wavelength for a matrix system employing two different concentration levels of erbium ions.

FIG. 19 plots fluorescent intensity in a.u. on the vertical axis and fluorescent wavelength in nm on the horizontal axis, for matrix 1460 employing two different concentration levels of erbium ions. Curve 1910 relates to an erbium concentration of 3 atomic percent, and curve 1920 relates to an erbium concentration of 1.5 atomic percent. Higher fluorescence was achieved with the lower erbium concentration, confirming that excessive erbium doping leads to self quenching.

Figure 20:
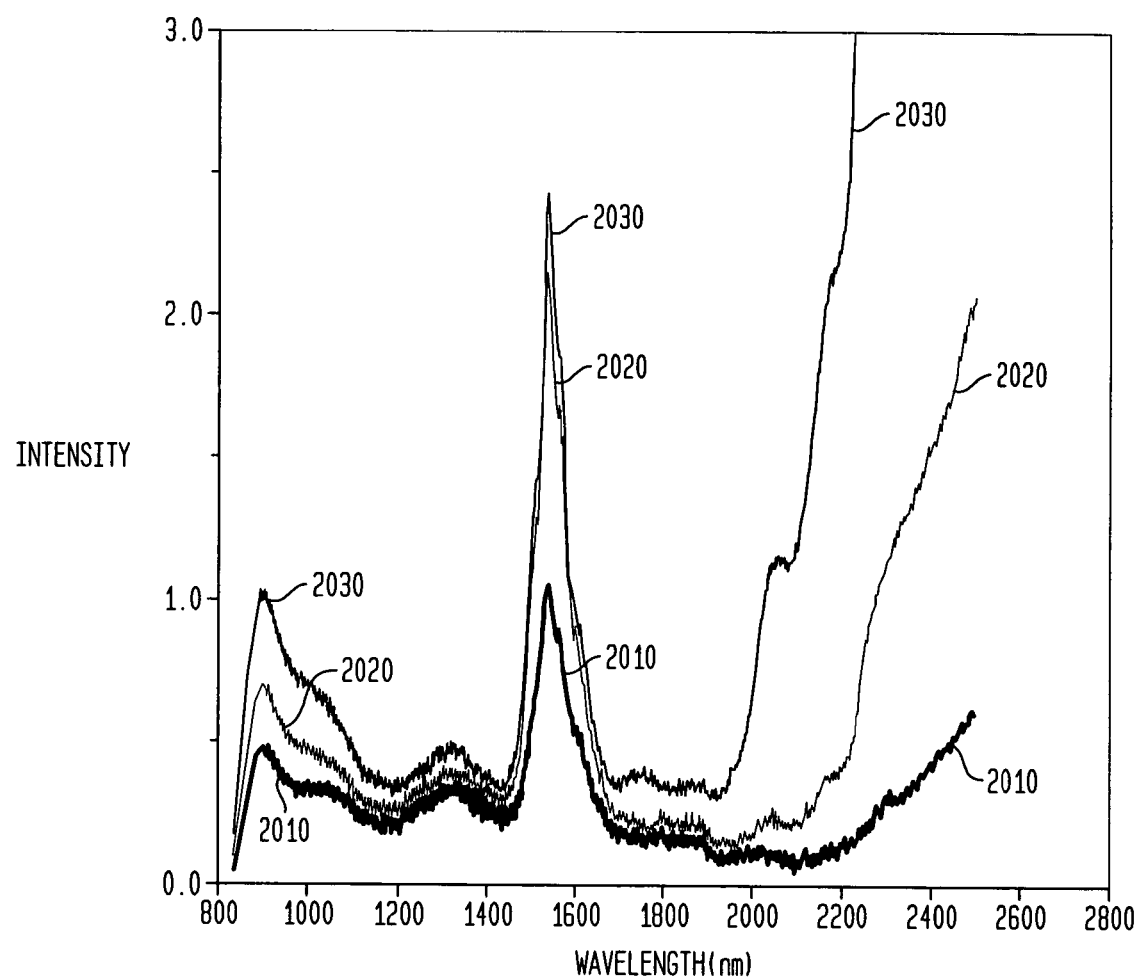
FIG. 20 shows graphed fluorescent intensity versus fluorescent wavelength for a matrix system employing three different argon laser power densities.

FIG. 20 plots fluorescent intensity in a.u. on the vertical axis and fluorescent wavelength in run on the horizontal axis, for matrix 1460 employing three different argon laser power densities. Curves 2010, 2020 and 2030 correspond to power densities of 1.5, 3.0 and 5.0 watts per square centimeter, respectively. The intensity appears to saturate when the power density approaches about 3 watts per square centimeter.

Figure 21:
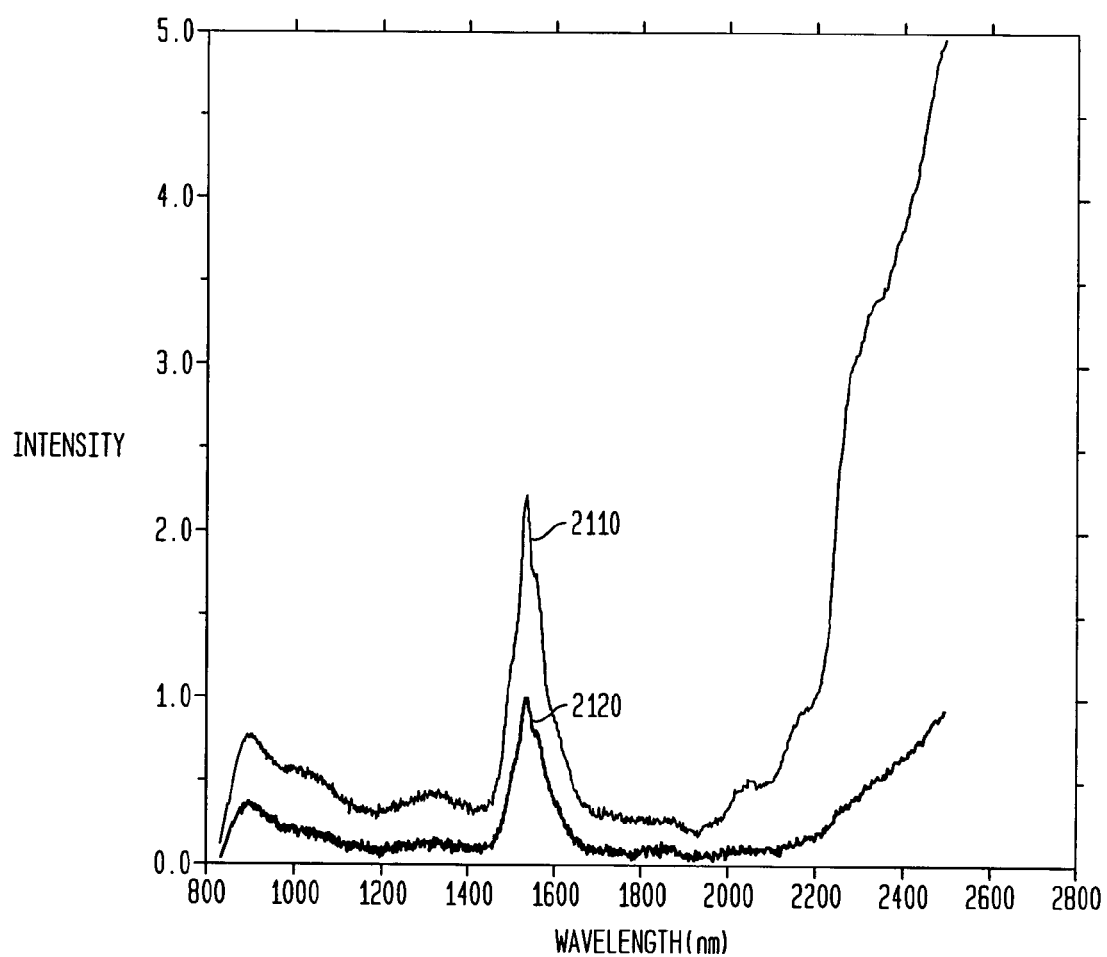
FIG. 21 shows graphed fluorescent intensity versus fluorescent wavelength for a matrix system prepared both with and without doping of cadmium selenide quantum dots.

FIG. 21 plots fluorescent intensity in a.u. on the vertical axis and fluorescent wavelength in nm on the horizontal axis, for matrix 1460 prepared both with and without doping of cadmium selenide quantum dots. Curves 2110 and 2120 correspond to embodiments with and without cadmium selenide quantum dots, respectively. Fluorescence is significantly increased by the addition of quantum dots.

Figure 22:
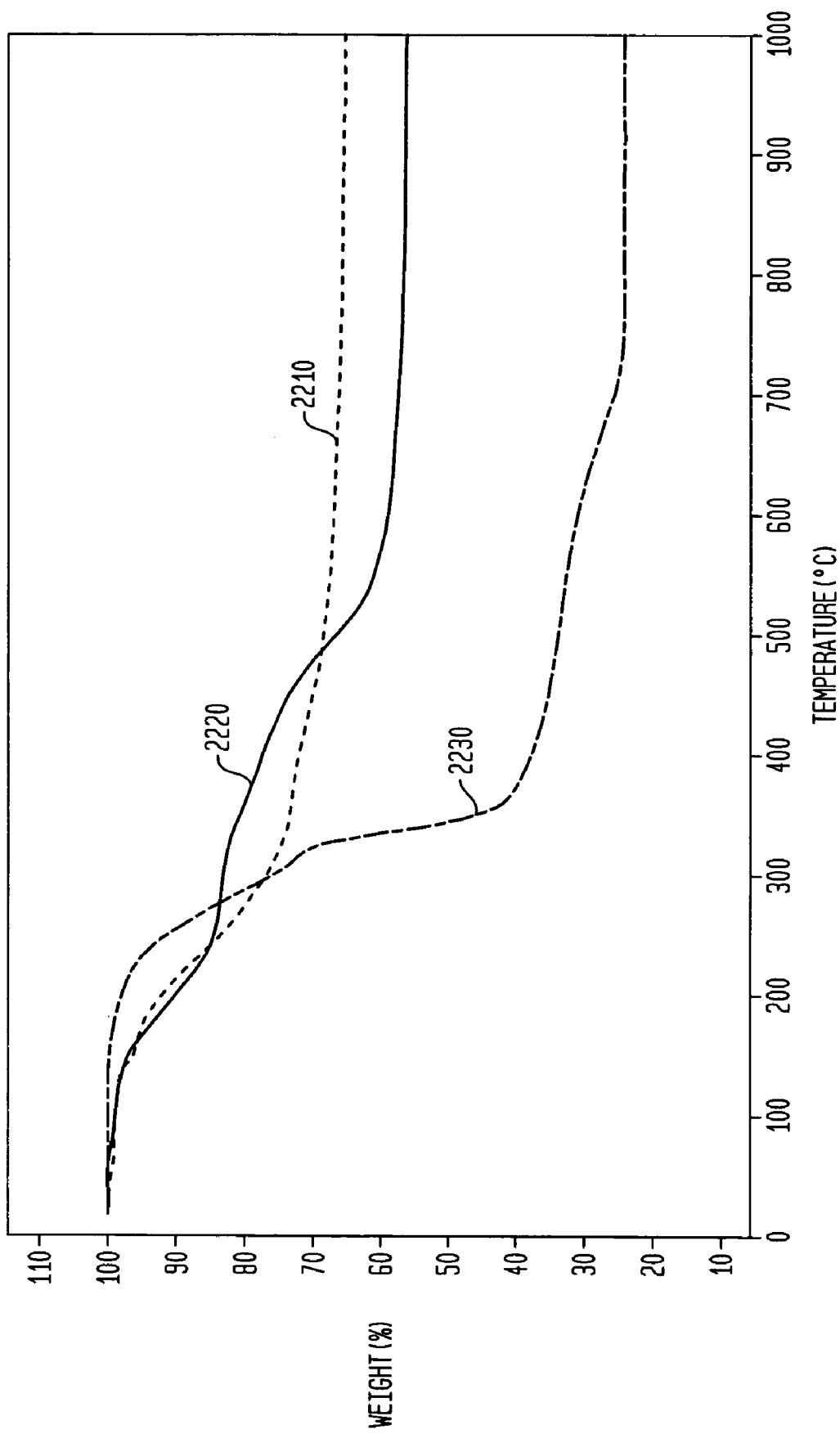
FIG. 22 shows graphed thermal stabilities of three matrix systems compared in connection with Example 4.

FIG. 22 shows the relative thermal stability of matrices 1440, 1450 and 1460 in curves 2210, 2220 and 2230, respectively. The vertical axis plots percentage weight loss and the horizontal axis plots temperature in degrees Centigrade. Data were obtained by using a Rheometric Scientific Inc. model No. PL-STA thermogravimeter. About 10 milligrams of each matrix were used for each experiment, heated under a nitrogen atmosphere in the temperature range of 25-1000° C. using a heating rate of 10° C. per minute. The TEOS based matrix 1440 showed a significant weight loss at 200-300° C. The bis(triethoxysilyl)hexane based matrix 1450 showed a somewhat complex weight loss pattern with a significant initial loss between about 150-225° C. The 2,2,3,3,4,4,5,5-octafluoro-1,6-hexanediol-bis(3-triethoxysilyl)propyl carbamate based matrix 1460 showed essentially no weight loss until reaching about 250° C., and then approximately 60% weight loss occurred over a temperature range of about 250-350° C.

EXAMPLE 5

Preparation of High Fluorine Host Matrix with Praseodymium Guests

Several grams each of the high-fluorine-content diene-end-functionalized reagent 1040 shown in FIG. 10 and triethoxysilane were thoroughly mixed together in a 1:2 molar ratio in a round bottom flask with isopropanol as solvent. The reaction between these reagents was allowed to take place over a period of about twenty hours at about 25° C. in the presence of a catalytic amount of chloroplatinic acid. The extent of reaction was monitored via GC analysis at periodic intervals. The resulting triethoxysilane end-terminated monomer product was recovered, analyzed and found to be 92.4% pure, then refrigerated.

A high-fluorine content polysilsesquioxane host matrix was then produced by condensation of the matrix precursor monomer prepared as reported in the preceding paragraph, in the presence of selected exemplary praseodymium atom-comprising guest molecule Pr(FOD)$_3$ having a structure consistent with FIG. 6 as discussed earlier. THF was thoroughly dried by distillation with stirring for several days using potassium as a drying agent. The matrix precursor monomer was mixed into THF at about a 0.4 molar concentration, and then about 5% by weight equivalent of the praseodymium atom-comprising guest molecule Pr(FOD)$_3$ was added. The condensation of the matrix precursor monomer was catalyzed by 7.5 molar % of either hydrochloric acid or sodium hydroxide, with about a six-fold stoichiometric excess of water. The resultant sols were then left to gel in glass vials at approximately 35° C. After gelation, the bridged polysilsesquioxanes were annealed at successively increasing temperatures ranging up to about 125° C. over two weeks. The degree of conversion of ethoxysilyl groups to —Si—O—Si— linkages in the polysilsesquioxane exceeded 95% by weight.

Fluorescent spectroscopy of the high fluorine content praseodymium-containing host matrix system discussed above was carried out by using a solid state neodymium-yttrium lithium fluoride (Nd:YLF) laser pump configuration. Gains in the range of about 20-40 decibels were observed over a range of pump powers. Fluorescent lifetimes observed for the 1300 nm transition ranged between about 80-140 microseconds. Gains were significantly enhanced by the incorporation of cadmium selenide semiconductor quantum dots.

EXAMPLE 6

Preparation of High Fluorine Host Matrix with Erbium Guests

Several grams each of the high-fluorine-content diene-end-functionalized reagent 1030 shown in FIG. 10 and triethoxysilane were thoroughly mixed together in a 1:2 molar ratio in a round bottom flask, with isopropanol as solvent. The reaction between these reagents was allowed to take place over a period of about twenty hours at about 25° C. in the presence of a catalytic amount of chloroplatinic acid. The extent of reaction was monitored via GC analysis at periodic intervals. The resulting triethoxysilane end-terminated monomer product was recovered and analyzed to confirm purity, and then refrigerated.

A high-fluorine content polysilsesquioxane host matrix was then produced by condensation of the matrix precursor monomer prepared as reported in the preceding paragraph, in the presence of TEOS and the selected exemplary erbium atom-comprising guest molecule $Er(FOD)_3$ having a structure consistent with FIG. 6 as discussed earlier. THF was thoroughly dried by distillation with stirring for several days using potassium as a drying agent. The matrix precursor monomer was mixed into THF at about a 0.4 molar concentration. A small amount of TEOS and about 5% by weight equivalent of the erbium atom-comprising guest molecule $Er(FOD)_3$ were added. The condensation reaction was catalyzed by 7.5 molar % of either hydrochloric acid or sodium hydroxide, with about a six-fold stoichiometric excess of water. The resultant sols were then left to gel in glass vials at approximately 35° C. After gelation, the bridged polysilsesquioxanes were annealed at successively increasing temperatures ranging up to about 125° C. over two weeks.

Fluorescent spectroscopy of the high fluorine content erbium host matrix system discussed above was carried out by using an argon ion laser. Significant gains were observed over a range of pump powers. From a range of analyses, it was found that the observed gains were controlled by system composition and erbium guest microenvironment. The gain was observed as being inversely correlated with erbium amount, and significantly enhanced by the incorporation of cadmium sulfide or cadmium selenide semiconductor quantum dots. The observed gain profiles also were progressively broadened and flattened via addition of ytterbium $(FOD)_3$ co-dopant.

Lanthanide metal based systems are increasingly of interest for photonic and optical applications in telecommunication and data-communication devices, networks and systems. Two arenas of increasing commercial relevance in telecommunications and data communications are optical amplification systems and upconversion laser systems.

An optical fiber amplifier is a device which directly amplifies an optical signal without the necessity of pre-amplification signal conversion to electricity and then post-amplification re-conversion to photons, as was previously the case in conventional optical fiber network based telecommunication systems. EDFAs, fabricated from inorganic silica glass materials doped with erbium, currently are firmly established as the preferred means of signal regeneration on long-haul telecommunication network links. Typically, pump laser light at 980 nm or 1490 nm, and an input signal at between 1530 nm and 1570 nm, are applied to an erbium doped optical fiber, resulting in amplification of the input signal. EDFAs are generally comprised of a rare-earth lanthanide-doped material integrated with other well-known components.

Figure 23:
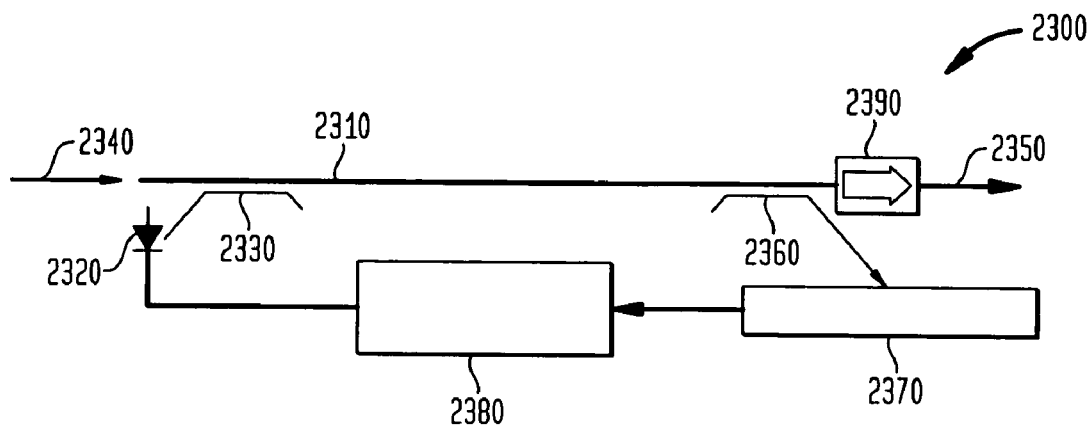
FIG. 23 shows an exemplary erbium doped fiber amplifier employing a polysesquioxane composition according to the present invention.

An exemplary EDFA system 2300 is shown in FIG. 23. The EDFA system 2300 includes an amplifier fiber 2310 doped with a selected polysesquioxane composition according to the present invention, a power laser 2320, a coupler 2330, an input optical fiber 2340, an output optical fiber 2350, a tap coupler 2360, a filter and detector unit 2370, a feedback power control unit 2380, and an isolator 2390. Amplifier fiber 2310 is compatible with the polysesquioxane composition and can be made, for example, from an organic plastic material. Input optical fiber 2340 is in optical communication with amplifier fiber 2310. Amplifier fiber 2310 is in optical communication with output optical fiber 2350 and interposed isolator 2390. Tap coupler 2360 is in optical coupling communication with amplifier fiber 2310 in the vicinity of output optical fiber 2350, and with filter and detector unit 2370. Feedback power control unit 2380 is in electrical communication with filter and detector unit 2370, and with power laser 2320. Power laser 2320 is in optical communication with amplifier fiber 2310 through coupler 2330 located near input optical fiber 2340. In operation, power laser 2320 applies pumping light via coupler 2330 to the amplifier fiber 2310. An input signal is directed by input optical fiber 2340 into amplifier fiber 2310. An amplified output signal is directed by output optical fiber 2350 toward its destination. Tap coupler 2360 directs a small portion of the amplified signal into filter and detector unit 2370, to produce an electrical feedback control signal which is then input to feedback power control unit 2380. Feedback power control unit 2380 controls the power level of power laser 2320 in order to maintain a desired level of amplification of the input signal. Isolator 2390 ensures one-way travel of the output signal. EDFAs typically include other well-known conventional components.

Commercial industrial focus has primarily been concentrated on erbium systems, although other lanthanide systems are also of interest. Lanthanide ions are able to exist in several energy states. With absorption of some external stimulation, lanthanide ions can be transformed from a lower energy ground state to a higher energy excited state. When a lanthanide ion is in a higher energy state, a photon of light will stimulate it to give up some portion of its energy as light, amplifying the original photon and thus returning the lanthanide to a more stable lower energy state. In operation, a high power beam of light from a pump laser typically is mixed with an input signal, and the mixed light is guided onto an erbium-rich inorganic glass material. This excites the erbium ions into a higher energy state. The photons belonging to the input signal, generally at a different wavelength from that of the pump laser, then interact selectively with the erbium ions. Energy transfer occurs such that the signal is amplified in the same phase and direction as that of the original input.

Erbium has four energy state levels, which in order of decreasing energy include levels $I_{9/2}$, $I_{13/2}$, $I_{11/2}$, and $I_{15/2}$. These energy state levels actually are groups of sub-states. The $I_{15/2}$ band possesses 8 sub-states, the $I_{11/2}$ band possesses 7 sub-states, the $I_{13/2}$ band possesses 6 sub-states, and the $I_{9/2}$ band possesses 5 sub-states. Electrons are free to occupy any sub-state within their current band, depending on their specific energy state, these sub-states being further broadened by thermal energy. As an electron is stimulated to jump between states, there are thus a wide range of energy levels available for it to occupy and therefore, an amplifier device can inherently exhibit an amplification effect over a relatively wide range. For example, where such a device is pumped with a 980 nm laser, a photon of light at 980 nm interacts with an electron in the $I_{15/2}$ state. The electron absorbs the photon energy and jumps to the $I_{13/2}$ band. The $I_{13/2}$ band is typically unstable and electrons there decay to the band just below the $I_{11/2}$ band, with the decay energy absorbed into lattice vibrations termed phonons. The $I_{11/2}$ state is metastable and, when an input signal photon eventually arrives and interacts with the excited electron, that electron as a result drops to one of the sub-states of the lower energy ground state. A photon is then given off with exactly the same phase, direction and wavelength as that of the input signal, resulting in signal amplification.

For a meaningful level of signal amplification, so-called inversion must exist, such that more erbium ions are within an excited state than are within the lower energy ground state. In this case, the statistical probability that an incoming signal photon will encounter an excited erbium ion is relatively high. In practice, inversion is ensured through continuous application of the pump laser, which constantly keeps erbium ions within an excited state. The amplifier gain is defined as the ratio in decibels of input signal power to post amplification output power. Generally, the gain of an amplifier varies with wavelength and thus is typically not flat or constant across a broad wavelength range, resulting in reduced efficiencies during operation. The use of additional co-dopants can significantly alter the opto-electronic response, leading to gain-flattening and enhanced performance across a range of operating wavelengths. Suitable co-dopants include, for example, yttrium, ytterbium, germanium and aluminum. For example, research has shown that co-dopant aluminum can broaden and flatten the gain spectrum of erbium systems over the 1540 nm to 1560 nm range, while co-dopant germanium can generate two gain peaks in the erbium system profile over a similar range.

The bridged polysesquioxane host matrices with incorporated guest molecules produced in accordance with the present invention can be formed into desired three dimensional structures using conventional solution processing techniques. For example, reaction injection molding, compression molding, extrusion molding, spin casting and micro stamping can be used. Where, for example, end use as the gain medium in an EDFA is desired, the polysesquioxane host matrices with incorporated guest molecules can be polymerized in place in a suitably shaped mold in order to produce a gelled, properly shaped material for incorporation into an amplifier fiber for a desired, appropriately configured amplifier system.

Figure 24:
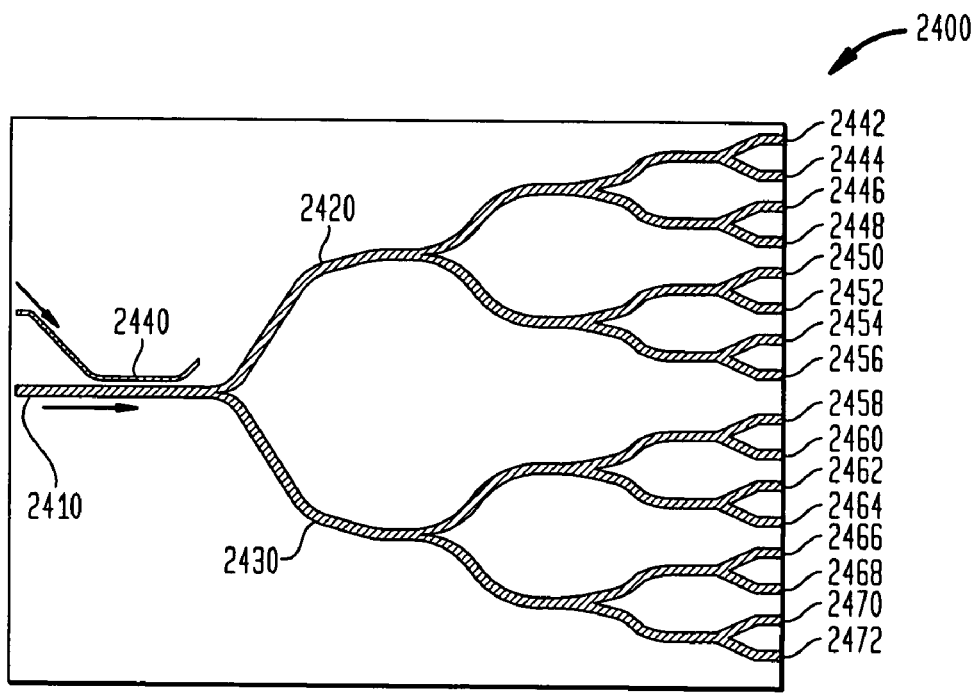
FIG. 24 shows an exemplary planar waveguide amplifier employing a polysesquioxane composition according to the present invention.

The discussion above has centered around optical fiber systems. However, the same principles apply to optical integrated circuits, which are micro-optical waveguide communication systems that are fabricated in planar architecture. These planar devices are the optical analogs to conventional microelectronic systems based around very large scale integrated (VLSI) silicon electronics. FIG. 24 shows an exemplary planar waveguide amplifier 2400. The planar waveguide amplifier 2400 includes a planar input waveguide 2410, amplifier fibers 2420 and 2430 which are doped with a selected polysesquioxane composition according to the present invention, a coupler 2440, and branched output waveguides 2442, 2444, 2446, 2448, 2450, 2452, 2454, 2456, 2458, 2460, 2462, 2464, 2466, 2468, 2470, and 2472. Amplifier fibers 2420 and 2430 are compatible with the polysesquioxane composition and can be made, for example, from an organic plastic material. Planar input waveguide 2410 is in optical communication with amplifier fibers 2420 and 2430, and in optical communication with coupler 2440. Amplifier fiber 2420 is in optical communication with a branched structure of waveguides terminating in output waveguides 2442-2456. Amplifier fiber 2430 is in optical communication with a branched structure of waveguides terminating in output waveguides 2458-2472. In operation, an input signal is provided on planar waveguide 2410 and directed into amplifier fibers 2420 and 2430. A power laser as discussed above in regard to FIG. 23 applies pumping light via coupler 2440 and planar waveguide 2410 to the amplifier fibers 2420 and 2430. Amplified output signals are directed by output waveguides 2442-2472 toward their destinations. The polysesquioxane host matrices according to the present invention can, for example, be spin cast into a thin layer which is then used to form the core of a photo-active planar waveguide fiber system.

The bridged polysesquioxane host matrices with incorporated guest molecules produced in accordance with the present invention can also be used in other applications requiring lanthanide-doped materials to serve as the medium for stimulated emission of a pump radiation amplified signal. For example, these polysesquioxane host matrices with incorporated guest molecules can be suitably shaped for use as the active medium for upconversion lasers. Upconversion fiber lasers are utilized to produce specific desired output signal wavelengths that are difficult to achieve using conventional media, materials and systems. The upconversion process is so-called because the energy level of photons produced is significantly higher, and the output light wavelength is shorter, than that of the pumping light. Lanthanides can be used as media in upconversion lasers and will lase at a desired wavelength, but typically are effective only by generating the high energy levels delivered by double pumping. Double pumping involves first pumping the lanthanide material to an intermediate metastable state, and then pumping it again with light at a different pumping wavelength to achieve a higher energy state, where lasing then occurs. For example, in-fiber blue lasers can be so constructed based on praseodymium doped systems with pumping at 835 nm and 1017 nm with blue light output generated at 492 nm.

Figure 25:
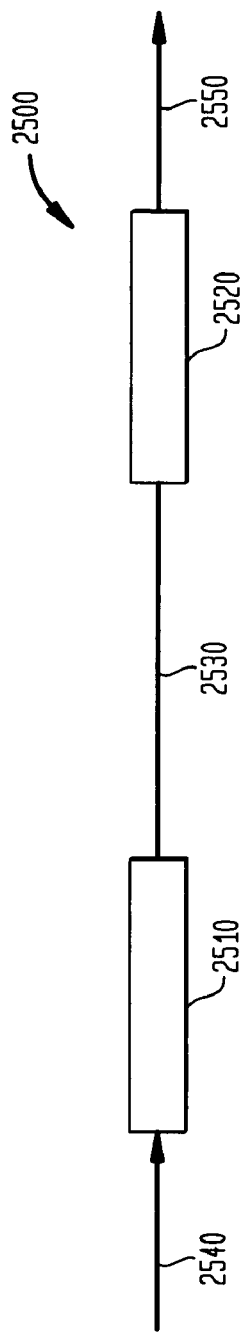
FIGS. 25 and 26 show exemplary embodiments of upconversion lasers employing a polysesquioxane composition according to the present invention.

An exemplary upconversion laser system 2500 is shown in FIG. 25. The exemplary double-pumped system 2500 comprises two fiber Bragg gratings (FBG) 2510 and 2520, a fiber section 2530 that is doped with a polysesquioxane composition according to the present invention, an input waveguide 2540, and an output waveguide 2550. Fiber section 2530 is compatible with the polysesquioxane composition and can be made, for example, from an organic plastic material. The input waveguide 2540 is in optical communication with FBG 2510, and the output waveguide 2550 is in optical communication with FBG 2520. The fiber section 2530 is in optical communication with FBGs 2510 and 2520. Pumping electromagnetic radiation is directed into the fiber section 2530 through input waveguide 2540, and laser light is directed toward a destination on output waveguide 2550. FBG 2510 effectively provides an 100% mirror preventing escape of light into input waveguide 2540 at the selected lasing wavelength. FBG 2520 effectively provides a selected mirror factor between about 5% and about 80% preventing premature escape of light into output waveguide 2550 at the selected lasing wavelength.

Figure 26:
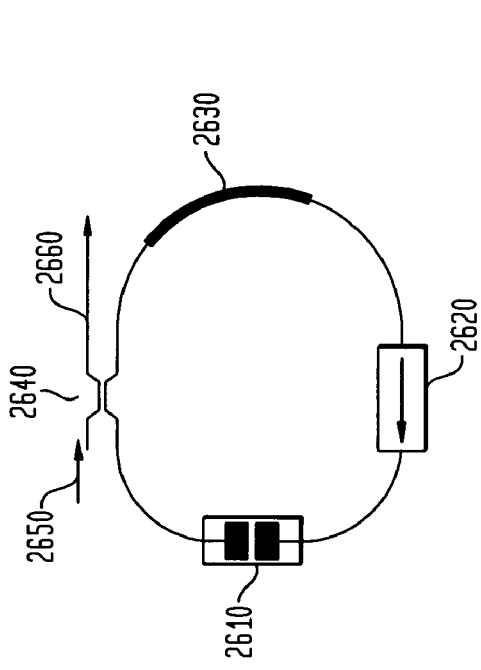

Other upconversion laser systems as well known in the laser system art can also incorporate the polysesquioxane compositions according to the present invention. For example, the polysesquioxane compositions according to the present invention can be incorporated into an upconversion fiber ring laser based on a fiber ring resonator system. FIG. 26 shows such an exemplary double-pumped system 2600. This system 2600 includes a Fabry-Perot device 2610, an isolator 2620, a fiber section 2630 doped with a polysesquioxane composition according to the present invention, a coupler 2640, an input waveguide 2650, and an output waveguide 2660. The fiber section 2630 is compatible with the polysesquioxane composition and can be made, for example, from an organic plastic material. The Fabry-Perot device 2610 comprises a light emitting diode with a pair of end mirrors, acting as a tunable filter to provide laser output light wavelength selectivity. The Fabry-Perot device 2610, the isolator 2620, and the fiber section 2630 are in mutual optical communication in a loop. The coupler is in optical communication with the loop at a point between the Fabry-Perot device 2610 and the fiber section 2630, and in optical communication with the input and output waveguides 2650 and 2660. Pumping radiation is input to fiber section 2630 on input waveguide 2650 via coupler 2640. Laser light is directed toward its destination on output waveguide 2660 via coupler 2640. The isolator 2620 eliminates generation of counter-propagating laser modes.

In sum, the polysesquioxane compositions according to the present invention may be applied to end use applications both as gain media and as upconversion laser media. Gain media applications can include both gain amplification of optical signals in organic plastic fibers, and in organic plastic-based planar waveguides. Upconversion laser materials can also be used in plastic laser systems.

The bridged polysesquioxane host matrices in accordance with the present invention can, in any of the foregoing applications, incorporate guest molecules containing lanthanides suitable to generate at least one fluorescence peak that is capable of amplifying light within at least one wavelength range selected from the group consisting of about 900-1000 nm, about 1260-1360 nm, and about 1500-1600 nm.

While the particular invention has been described with reference to illustrative embodiments, this description is not meant to be construed in a limiting sense. It is understood that although the present invention has been described, various modifications of the illustrative embodiments, as well as additional embodiments of the invention, will be apparent to one of ordinary skill in the art upon reference to this description without departing from the spirit of the invention, as recited in the claims appended hereto. For example, the polysesquioxane compositions disclosed herein may be modified to contain different metallic elements, electron withdrawing and donating moieties, guest molecules, co-dopants, and semiconductor quantum-dot particles consistent with this disclosure. The carbon chains within such polysesquioxanes may be of any desired length and may optionally include branching, unsaturation, heteroatoms, and further substituents consistent with this disclosure. Additional guest molecule structures suitable for chelating lanthanides and for themselves being chelated by the polysesquioxane host matrices can further be designed and synthesized consistent with this disclosure. Further, the polysesquioxane compositions may be used in making gain media and active materials for use in devices other than the fiber amplifiers and upconversion lasers disclosed herein. Those skilled in the art will readily recognize that these and various other modifications, arrangements and methods can be made to the present invention without strictly following the exemplary applications illustrated and described herein and without departing from the spirit and scope of the present invention. It is therefore contemplated that the appended claims will cover any such modifications or embodiments as fall within the true scope of the invention.

I claim:

1. A bridged polysesequioxane composition comprising: a bridged polysesquioxane host matrix comprising sesquioxane moieties and organic moieties, said sesquioxane moieties comprising a metallic element, said organic moieties interposed between sesquioxane moieties; and a guest molecule comprising a lanthanide atom; at least some of said organic moieties comprising a substituent selected from the group consisting of electron withdrawing functional groups and electron donating functional groups; in which said guest molecule is a compound having Formula 1 below,

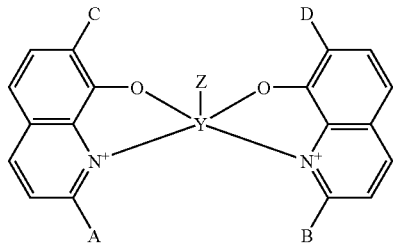

in which A, B, C and D each independently can be hydrogen or -alkyl; Y is a lanthanide atom; and Z is an oxyaryl group.

2. The composition of claim 1 in which Z is an aromatic moiety selected from the group consisting of: phenolic, alkylphenolic, hydroxynaplithalenyl, alkylhydroxynaphthalenyl, 8-hydroxyquinolinyl, and alkyl-8-hydroxyquinolinyl.

3. A gain medium comprising the composition of claim 1, in which the composition has a fluorescence peak that is capable of amplifying light within at least one wavelength range selected from the group consisting of 900-1000 nanometers, 1260-1360 nanometers, and 1500-1600 nanometers.

4. An active material for an upconversion laser comprising the composition of claim 1, in which the composition has a fluorescence peak that is capable of amplifying light within at least one wavelength range selected from the group consisting of 900-1000 nanometers. 1260-1360 nanometers, and 1500-1600 nanometers.

5. The composition of claim 1, including organic moieties having either or both of an electron withdrawing functional group and an electron donating functional group, wherein the electron withdrawing functional group is selected from the group consisting of —CN, SO$_3$H, haloalkyl, haloalkenyl, or haloalkynyl; and wherein the electron donating functional group is selected from the group consisting of a urethane group, an amide group, or: —NR$_2$, —NH$_2$, —NRH, —OR, —PR$_2$, —PH$_2$, or —PRH, in which R is a lower alkyl.

6. A process for making a bridged polysesquioxane composition comprising the steps of: providing a bridged polysesquioxane host matrix comprising sesquioxane moieties arid organic moieties, said sesquioxane moieties comprising a metallic element, said organic moieties interposed between sesquioxane moieties; and providing a guest molecule comprising a lanthanide atom; at least some of said organic moieties comprising a substituent selected from the group consisting of electron withdrawing functional groups and electron donating functional groups; in which said guest molecule is a compound having Formula 1 below,

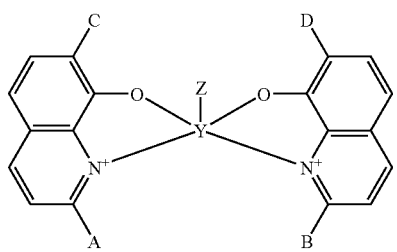

in which A, B, C and D each independently can be hydrogen or -alkyl; Y is a lanthanide atom; and Z is an oxyaryl group.

7. The process of claim 6 in which Z is an aromatic moiety selected from the group consisting of: phenolic, alkylphenolic, hydroxynaphthalenyl, alkylhydroxynaphthalenyl, 8-hydroxyquinolinyl, and alkyl-8-hydroxyquinolinyl.

8. The process of claim 6, wherein organic moieties have either or both of an electron withdrawing functional group and an electron donating functional group, wherein the electron, withdrawing functional group is selected from the group consisting of —CN, $SO_3H$, haloalkyl, haloalkenyl, or haloalkynyl; and wherein the electron donating functional group is selected from the group consisting of a urethane group, an amide group, or: —$NR_2$, —$NH_2$, —NRH, —OR, —$PR_2$, —$PH_2$, or PRH, in which R is a lower alkyl.

* * * * *